United States Patent
Shimizu et al.

(10) Patent No.: US 9,696,274 B2
(45) Date of Patent: Jul. 4, 2017

(54) GAS SENSOR ELEMENT AND GAS SENSOR

(71) Applicant: NGK Spark Plug Co., Ltd., Nagoya-shi, Aichi-ken (JP)

(72) Inventors: Yasumitsu Shimizu, Kiyosu (JP); Seiji Oya, Niwa-gun (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 142 days.

(21) Appl. No.: 14/613,251

(22) Filed: Feb. 3, 2015

(65) Prior Publication Data

US 2015/0219591 A1 Aug. 6, 2015

(30) Foreign Application Priority Data

Feb. 6, 2014 (JP) ................... 2014-021190

(51) Int. Cl.
*G01N 27/407* (2006.01)
*G01N 27/409* (2006.01)
*G01N 27/41* (2006.01)

(52) U.S. Cl.
CPC ....... *G01N 27/4071* (2013.01); *G01N 27/409* (2013.01); *G01N 27/4072* (2013.01); *G01N 27/4073* (2013.01); *G01N 27/41* (2013.01)

(58) Field of Classification Search
CPC .......... G01N 27/4071; G01N 27/4072; G01N 27/4073; G01N 27/409; G01N 27/41
See application file for complete search history.

(56) References Cited

U.S. PATENT DOCUMENTS

| | | | |
|---|---|---|---|
| 2009/0188620 A1* | 7/2009 | Okuda | B32B 18/00 156/277 |
| 2011/0233060 A1* | 9/2011 | Horisaka | G01N 27/419 204/412 |
| 2011/0240469 A1* | 10/2011 | Watanabe | G01N 27/4071 204/424 |
| 2013/0019655 A1* | 1/2013 | Nakagawa | G01N 27/419 73/31.05 |
| 2014/0332378 A1* | 11/2014 | Nakasone | G01N 27/41 204/410 |

FOREIGN PATENT DOCUMENTS

| | | | |
|---|---|---|---|
| JP | 3635191 B2 | | 1/2005 |
| JP | 3635191 B2 | * | 4/2005 |
| JP | 4223471 B2 | | 11/2008 |
| JP | 4223471 B2 | * | 2/2009 |

* cited by examiner

*Primary Examiner* — Keith Hendricks
*Assistant Examiner* — Joshua Allen
(74) *Attorney, Agent, or Firm* — Stites & Harbison, PLLC; Jeffrey A. Haeberlin; James R. Hayne

(57) ABSTRACT

A gas sensor element of an air/fuel ratio sensor has a structure in which at least a part of an end portion of a porous electrode is sandwiched between a porous member and a solid electrolyte member. Therefore, it is possible to restrain shrinkage of the porous electrode during manufacture of the gas sensor element, which shrinkage would otherwise occur at the time of heating in a debindering step or at the beginning of a firing step, whereby occurrence of green breakage in the solid electrolyte member is restrained. Thus, cracking due to green breakage is restrained from occurring in the solid electrolyte member produced through firing. Since the end portion of the porous electrode can receive oxygen through the porous member, blackening of the solid electrolyte member can be prevented.

9 Claims, 13 Drawing Sheets

GAS SENSOR ELEMENT AND GAS SENSOR

CROSS REFERENCE TO RELATED APPLICATION

The present application claims priority from Japanese Patent Application No. 2014-021190, which was filed on Feb. 6, 2014, the disclosure of which is herein incorporated by reference in its entirety.

BACKGROUND OF THE INVENTION

Field of the Invention

The present invention relates to a gas sensor element for detecting a particular gas contained in gas to be measured, and a gas sensor having such a gas sensor element.

Description of Related Art

An example of a conventionally known gas sensor having a gas sensor element for detecting a particular gas contained in gas to be measured is an oxygen sensor installed in an exhaust flow path, such as an exhaust pipe of an internal combustion engine, and utilized in controlling combustion of the internal combustion engine through detection of the oxygen concentration of exhaust gas. Other examples of such a gas sensor include a NOx sensor for detecting NOx concentration and an air/fuel ratio sensor for detecting the ratio between air and fuel, etc.

Such a gas sensor has, for example, a tubular metallic shell, and a gas sensor element held in the metallic shell.

The gas sensor element may be a plate-shaped gas sensor element. The plate-shaped gas sensor element includes a plate-shaped solid electrolyte member having a pair of electrodes disposed on the surface thereof, and a dense member which is stacked on the solid electrolyte member and forms at least a portion of a wall surface of a hollow cavity into which gas to be measured or the atmosphere is introduced.

Notably, the gas sensor element is manufactured by firing a green (unfired) laminate formed of ceramic. The green laminate is formed by providing, by means of printing and laminating, on a green solid electrolyte sheet which is to become the solid electrolyte member, green electrodes which are formed primarily of metal and are to become the electrodes, a green wall surface sheet which is to become the wall surface of the hollow cavity, etc.

Such a gas sensor element has the following problem. At the time of manufacture, small damage (green breakage) may occur in the green solid electrolyte sheet due to volume shrinkage occurring as a result of heating in a debindering step or the difference in thermal shrinkage between ceramic and metal caused by a change in temperature at the beginning of a firing step. In some situations, due to a thermal shock, a portion where such a green breakage has occurred becomes a start point of cracking, and a crack is produced in a solid electrolyte member formed through firing. In such a case, the function of the gas sensor element is impaired.

In order to solve such a problem, there has been proposed a gas sensor element which restrains shrinkage of a green electrode to thereby restrain green breakage through employment of a structure in which an end portion of an electrode is held and covered by a dense member (Patent Document 1).

RELATED ART DOCUMENTS

Patent Document 1 is Japanese Patent No. 4223471.
Patent Document 2 is Japanese Patent No. 3635191.

BRIEF SUMMARY OF THE INVENTION

However, the above-mentioned conventional gas sensor element has the following problem: the supply of oxygen to the portion of the electrode held and covered by the dense member may become insufficient, and consequently, blackening may occur on the solid electrolyte member.

For example, a gas sensor element 507 shown in FIG. 18 is configured such that end portions of a porous electrode 587 are sandwiched between an insulating spacer 593 and a solid electrolyte member 583. Therefore, blackening may occur on the solid electrolyte member 583 in regions 584 adjacent to the end portions of the porous electrode 587. Notably, in the gas sensor element 507, the porous electrode 587 and another porous electrode 585 are laminated on the solid electrolyte member 583, and a hollow cavity 591 is formed by the solid electrolyte member 583, the insulating spacer 593, and an insulating member 596.

Notably, blackening is a phenomenon in which the color of a solid electrolyte member changes (changes to pale yellow to black) and in which the crystalline structure becomes irregular as a result of removal of oxygen from the solid electrolyte member. A solid electrolyte member having suffered blackening may exhibit electron conductivity and lower sensor accuracy. In the case where the blackening is sever, the blacking serves as the start point of cracking.

A conceivable way to restrain such blackening is replacing the dense members which sandwich the end portions of the electrode with porous members so as to supply oxygen to the end portions of the electrode. For example, there can be employed a structure shown in Patent Document 2 in which an end portion of an electrode is sandwiched between a porous member (first diffusion resistance member) and a solid electrolyte layer.

However, the gas sensor element disclosed in Patent Document 2 has the following problem: since an end portion of the electrode reaches the interface between the porous member and the dense member and the electrode is in contact with the dense member, "green breakage" may occur in the solid electrolyte member in a region where the electrode is in contact with the dense member. In particular, since the electrode and the dense member differ in material and therefore differ in the amount of thermal shrinkage, "green breakage" may occur in the solid electrolyte member in a region where the electrode is in contact with the dense member.

In view of the foregoing problem, an object of the present invention is to provide a gas sensor element which can prevent blackening of a solid electrolyte member and can prevent green breakage of the solid electrolyte member at the time of manufacture to thereby prevent cracking of the solid electrolyte member produced through firing. Another object of the present invention is to provide a gas sensor having such a gas sensor element.

(1) A gas sensor element according to a first aspect of the present invention includes a solid electrolyte member and a ceramic dense member (also simply referred to as a dense member) and is adapted to detect a particular gas contained in a gas to be measured, wherein a ceramic porous member (also simply referred to as a porous member) is provided in a hollow cavity so as to sandwich at least a part of an end portion of a cavity side electrode in cooperation with the solid electrolyte member.

Notably, the solid electrolyte member is a plate-shaped ceramic member having a pair of electrodes formed primarily of a metal and disposed on the solid electrolyte member; and the dense member is layered on the solid electrolyte member and forms or defines at least a portion of a wall surface of the hollow cavity into which the gas to be measured or the atmosphere is introduced.

The cavity side electrode is one of the pair of electrodes, and is disposed to face the hollow cavity. The cavity side electrode is disposed such that it is spaced from the dense member, for example the cavity side electrode is spaced from the portion of the wall surface of the hollow cavity that is formed by the ceramic dense member.

The gas sensor element includes the porous member provided in the hollow cavity and partially covering the cavity side electrode. The porous member is a ceramic member which extends from a position on the cavity side electrode, beyond an end or peripheral edge portion of the cavity side electrode to a position on a surface of the solid electrolyte member exposed to the hollow cavity. In other words, the end or peripheral edge portion of the cavity side electrode is at least partially or completely covered by the porous member, and the end or peripheral edge portion of the cavity side electrode remains spaced from the portion of the wall surface of the hollow cavity, particularly from the sidewall portions of the hollow cavity, which are formed by the ceramic dense member.

The porous member is arranged in the hollow cavity which is typically defined by the solid electrolyte member and the dense member.

According to an embodiment, which can be combined with other embodiments described herein, the porous member can be formed to cover only the end or peripheral edge portion of the cavity side electrode while leaving a central portion of the cavity side electrode uncovered.

According to an embodiment, which can be combined with other embodiments described herein, the porous member can be formed to cover completely the cavity side electrode without providing a hollow chamber adjacent to the cavity side electrode.

According to an embodiment, which can be combined with other embodiments described herein, the porous member can be formed from a single part, which can have, for example a ring-like shape or can be U-shaped.

According to an embodiment, which can be combined with other embodiments described herein, the gas sensor element can include a first and a second porous member which are spaced from each other, for example to cover only opposite ends or portions of the peripheral edge portion of the cavity side electrode while leaving a central portion of the cavity side electrode uncovered.

The dense member can be formed, for example, by an insulating spacer or by an insulating spacer and an insulating substrate.

Namely, since at least a part of an end portion or peripheral edge portion of the cavity side electrode is sandwiched between the solid electrolyte member and the porous member, movement (movement due to shrinkage) of the sandwiched portion of the cavity side electrode is restrained. Therefore, it is possible to prevent shrinkage of the cavity side electrode at the time of manufacture, which shrinkage would otherwise occur at the time of heating in a debindering step or at the beginning of a firing step. Thus, occurrence of green breakage in the solid electrolyte member can be prevented. Accordingly, occurrence of cracking due to green breakage can be prevented from occurring in the solid electrolyte member produced through firing.

Also, since the end portion of the cavity side electrode is sandwiched between the solid electrolyte member and the porous member, the end portion of the cavity side electrode can receive oxygen through the porous member, unlike a structure in which the end portion of the cavity side electrode is sandwiched between a dense member and a solid electrolyte member. Therefore, shortage of oxygen is unlikely to occur, and blackening of the solid electrolyte member can be prevented.

Further, the cavity side electrode is disposed such that it is spaced from the dense member, particularly from sidewall portions of the hollow cavity which are formed by the ceramic dense member. Since there does not exist a region where the cavity side electrode is in contact with the dense member, it is possible to prevent generation of stress in the solid electrolyte member, which stress would otherwise be generated due to the difference in shrinkage amount between the cavity side electrode and the dense member. Therefore, it is possible to prevent occurrence of "green breakage" in the solid electrolyte member, which would otherwise occur due to the difference in shrinkage amount between the cavity side electrode and the dense member. As a result, it is possible to prevent cracking of the solid electrolyte member obtained through firing.

Therefore, according to the gas sensor element of the present invention, it is possible to restrain blackening of the solid electrolyte member and restrain green breakage of the solid electrolyte member at the time of manufacture, to thereby prevent cracking of the solid electrolyte member produced through firing.

(2)(3) A gas sensor element according to another aspect of the present invention may employ a structure in which the ceramic porous member for partially covering the cavity side electrode includes at least two separate ceramic porous members, or in which the ceramic porous member for partially covering the cavity side electrode is formed by at least two sections. The sections or the two ceramic members are provided at two positions corresponding to opposite ends of the cavity side electrode in a longitudinal direction thereof, and the opposite ends of the cavity side electrode are sandwiched between the porous members and the solid electrolyte member. The ceramic porous member can be formed by at least two sections which are connected to form a shaped ceramic porous member such as a U-shaped or ring-shaped ceramic members. The at least two sections can form the legs of the U-shaped ceramic porous member. In case of a ring-shaped ceramic porous member, the at least two sections can form two opposite portions of the ring-like shape.

In the case where the cavity side electrode shrinks in the debindering step or at the beginning of the firing step, the amount of shrinkage of the cavity side electrode in the longitudinal direction becomes larger than the amount of shrinkage of the cavity side electrode in a direction orthogonal to the longitudinal direction. Therefore, green breakage of the solid electrolyte member becomes more likely to occur at opposite ends of the cavity side electrode in the longitudinal direction.

In consideration of this, there is employed a structure in which each of the opposite ends of the cavity side electrode in the longitudinal direction is sandwiched between the porous member and the solid electrolyte member. Thus, green breakage of the solid electrolyte member can be prevented more effectively.

(4) A gas sensor element according to still another aspect of the present invention may have a structure in which a porous diffusion resistance portion is provided in a gas introduction passage extending from an outer wall surface of the gas sensor element to the hollow cavity, wherein the porous member has a diffusion resistance equal to or smaller than that of the diffusion resistance portion.

Namely, in the case where the diffusion resistance of the porous member is equal to or smaller than the diffusion resistance of the diffusion resistance portion, diffusion of a particular gas (for example, oxygen) is not controlled or limited in the porous member. As a result, the amount of the particular gas (for example, oxygen) supplied through the porous member can be made sufficiently large, and blackening of the solid electrolyte member can be restrained to a greater degree.

(5) A gas sensor element according to still another aspect of the present invention may have a structure in which the cavity side electrode is a porous electrode, and has a diffusion resistance equal to or larger than that of the porous diffusion resistance portion.

In the case where the diffusion resistance of the cavity side electrode is equal to or larger than the diffusion resistance of the diffusion resistance portion as described above, diffusion of the particular gas (for example, oxygen) at the cavity side electrode can be controlled or limited, whereby pumping of the particular gas (for example, oxygen) by the cavity side electrode can be properly realized.

As a result, the accuracy in detecting the particular gas by the gas sensor element can be increased.

(6) In a gas sensor element according to still another aspect of the present invention, the hollow cavity may be a measuring chamber into which the gas to be measured is introduced.

(7) In a gas sensor element according to still another aspect of the present invention, the hollow cavity may be an atmospheric chamber into which the atmosphere is introduced.

(8) A gas sensor according to still another aspect of the present invention comprises any one of the above-described gas sensor elements as a gas sensor for detecting a particular gas contained in gas to be measured.

A gas sensor which includes any one of the above-described gas sensor elements can prevent blackening of the solid electrolyte member of the gas sensor element, and can prevent green breakage of the solid electrolyte member at the time of manufacture of the gas sensor element to thereby prevent cracking of the solid electrolyte member produced through firing.

The gas sensor element and the gas sensor of the present invention can prevent blackening of the solid electrolyte member, and can prevent green breakage of the solid electrolyte member at the time of manufacture to thereby prevent cracking of the solid electrolyte member produced through firing.

DETAILED DESCRIPTION OF EXEMPLARY EMBODIMENTS OF THE INVENTION

Preferred embodiments of the present invention will next be described with reference to the drawings.

The following embodiments will be described while referring to a full range air/fuel ratio sensor (hereinafter, may be referred to merely as the air/fuel ratio sensor), which is a kind of oxygen sensor among gas sensors. Specifically, the following description will refer to an air/fuel ratio sensor which is used for air/fuel ratio feedback control in automotive internal combustion engines and other various types of internal combustion engines. Such an air/fuel ratio sensor is attached to an exhaust pipe of an internal combustion engine and includes a gas sensor element (detecting element) for detecting a particular gas (oxygen) contained in gas to be measured; specifically, exhaust gas.

1. First Embodiment 1-1. Overall Configuration

Figure 1:
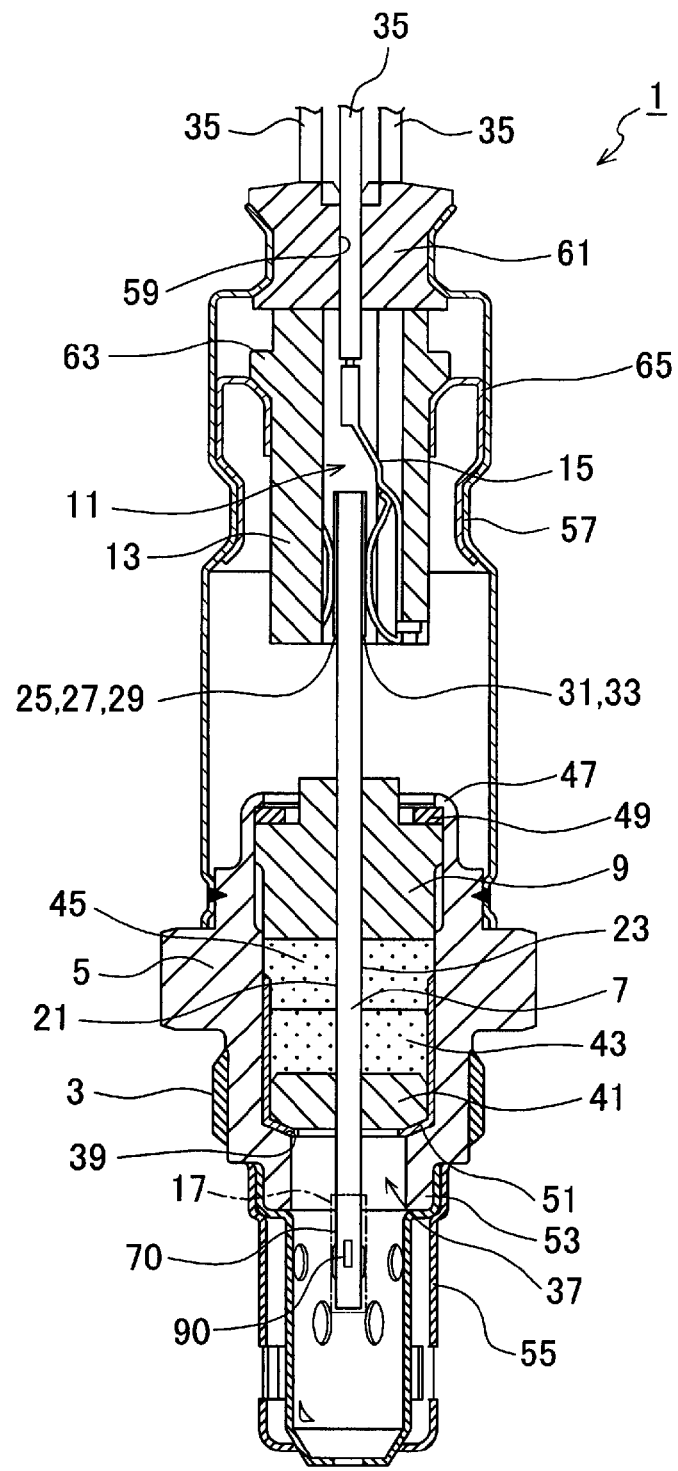
FIG. 1 is a sectional view of an air/fuel ratio sensor according to an embodiment taken along an axial direction.

The overall configuration of an air/fuel ratio sensor which uses a gas sensor element of the present embodiment will be described with reference to FIG. 1. FIG. 1 is a sectional view showing the internal structure of the air/fuel ratio sensor.

As shown in FIG. 1, an air/fuel ratio sensor 1 of the present embodiment includes a tubular metallic shell 5 having a threaded portion 3 formed on its outer surface and adapted to fix it to an exhaust pipe; a plate-shaped gas sensor element 7 extending in an axial direction (a longitudinal direction of the air/fuel ratio sensor 1, a vertical direction in FIG. 1); a tubular ceramic sleeve 9 disposed in such a manner as to radially surround the gas sensor element 7; an insulating contact member 13 (separator 13) which has an insertion hole 11 extending therethrough in the axial direction and which is disposed such that the inner wall surface of the insertion hole 11 surrounds a rear end portion of the gas sensor element 7; and five connection terminals 15 (FIG. 1 shows only two of them) disposed between the gas sensor element 7 and the separator 13.

As will be described in detail later, the gas sensor element 7 includes a rectangular-parallelepiped element body 70 extending in the longitudinal direction, and a porous protection layer 17 which covers a forward end portion of the element body 70. The element body 70 has a detecting section 90 provided in its forward end region and adapted to detect a particular gas contained in gas to be measured. Also, the gas sensor element 7 has electrode pads 25, 27, 29, 31, and 33 formed on the outer surface of its rear end portion (an upper end portion in FIG. 1, a longitudinally rear end portion); specifically, on a first main surface 21 and a second main surface 23 of the rear end portion which are located on the front and back sides of the gas sensor element 7 (see FIGS. 2 and 3 for detail).

The connection terminals 15 are electrically connected to the electrode pads 25, 27, 29, 31, and 33, respectively, of the gas sensor element 7, and are also electrically connected to respective lead wires 35 extending into the sensor from outside, thereby forming electrical current paths through which electric current flows between an external device connected to the lead wires 35, and the electrode pads 25, 27, 29, 31, and 33.

The metallic shell 5 has a substantially tubular shape and is configured to have a through hole 37 extending therethrough in the axial direction and a ledge 39 protruding radially inward from the wall surface of the through hole 37. The metallic shell 5 holds the gas sensor element 7 inserted through the through hole 37 in such a manner that the detecting section 90 is disposed forward of the forward end of the through hole 37, while the electrode pads 25, 27, 29, 31, and 33 are disposed rearward of the rear end of the through hole 37.

Also, in the through hole 37 of the metallic shell 5, an annular ceramic holder 41, a talc ring 43, a talc ring 45, and the ceramic sleeve 9 are stacked rearward in this order in such a manner as to radially surround the gas sensor element 7.

A crimp packing 49 is disposed between the ceramic sleeve 9 and a rear end portion 47 of the metallic shell 5, while a metallic holder 51 for holding the talc ring 43 and the ceramic holder 41 is disposed between the ceramic holder 41 and the ledge 39 of the metallic shell 5. The rear end portion 47 of the metallic shell 5 is crimped in such a manner as to press forward the ceramic sleeve 9 through the crimp packing 49.

Furthermore, a protector 55 made of metal (e.g., stainless steel) and having a dual structure is attached to the outer circumference of a forward end portion 53 of the metallic shell 5 by, for example, welding and covers a protruding portion of the gas sensor element 7.

Meanwhile, an outer tube 57 is fixed to the outer circumference of a rear portion of the metallic shell 5. A grommet 61 having lead wire insertion holes 59 formed therein is disposed in a rear opening of the outer tube 57, and the five lead wires 35 (FIG. 1 shows three of them) are inserted through the respective lead wire insertion holes 59 and are electrically connected to the electrode pads 25, 27, 29, 31, and 33, respectively.

The separator 13 has a collar portion 63 formed along its outer circumference, and the collar portion 63 is fixed to the outer tube 57 through a holding member 65.

1-2. Configuration of Gas Sensor Element

Next, the structure of the gas sensor element 7, which is an essential member of the present embodiment, will be described in detail with reference to FIGS. 2 to 5.

Figure 2:
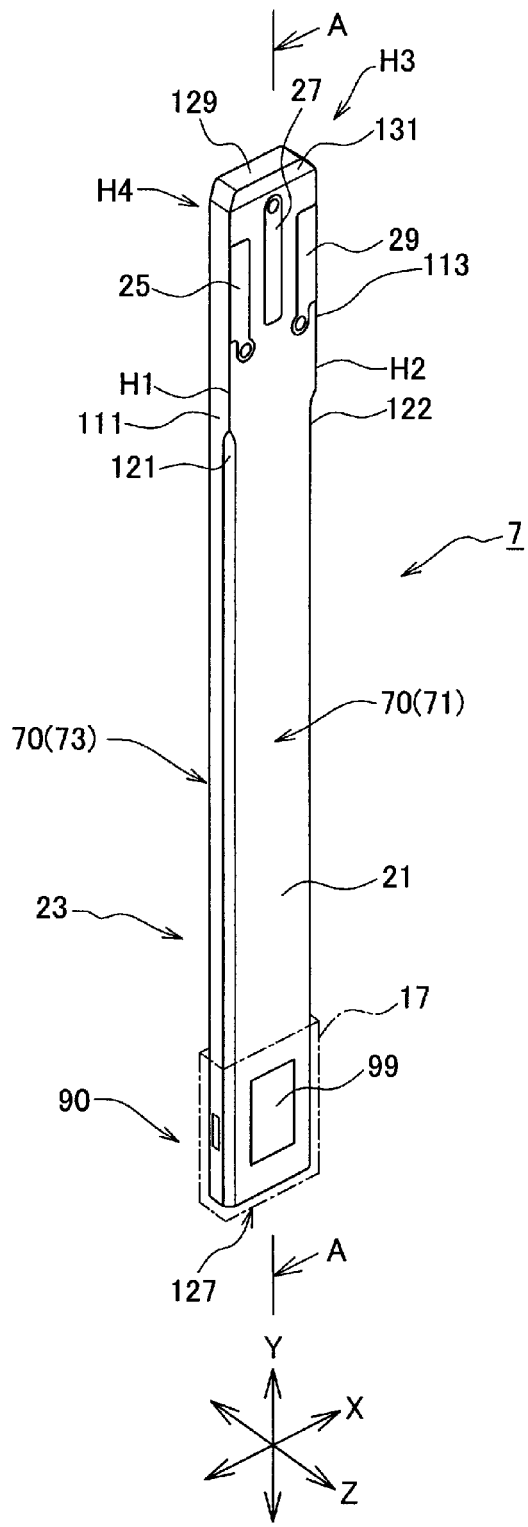
FIG. 2 is a perspective view showing a gas sensor element.

FIG. 2 is a perspective view showing the appearance of the gas sensor element 7.

As shown in FIG. 2, the gas sensor element 7 is an elongated plate member extending in the longitudinal direction (Y-axis direction). In FIG. 2, the longitudinal direction corresponds to the axial direction of the gas sensor. Also, in FIG. 2, a Z-axis direction is a thickness direction perpendicular to the longitudinal direction, and an X-axis direction is a width direction perpendicular to the longitudinal direction and to the thickness direction.

The gas sensor element 7 includes a rectangular-parallelepiped element body 70 extending in the longitudinal direction, and the porous protection layer 17 which covers a forward end portion (a lower end portion in FIG. 2) of the element body 70. The element body 70 is configured such that a plate-shaped element 71 extending in the longitudinal direction and a plate-shaped heater 73 extending in the longitudinal direction are laminated together. The element body 70 has the detecting section 90 provided in its forward end region and adapted to detect a particular gas contained in gas to be measured. The protection layer 17 is provided on a forward end surface 127 and side surfaces (the first main surface 21, the second main surface 23, a first side surface 111, and a second side surface 113) of the element body 70 in such a manner as to cover at least the detecting section 90.

Figure 3:
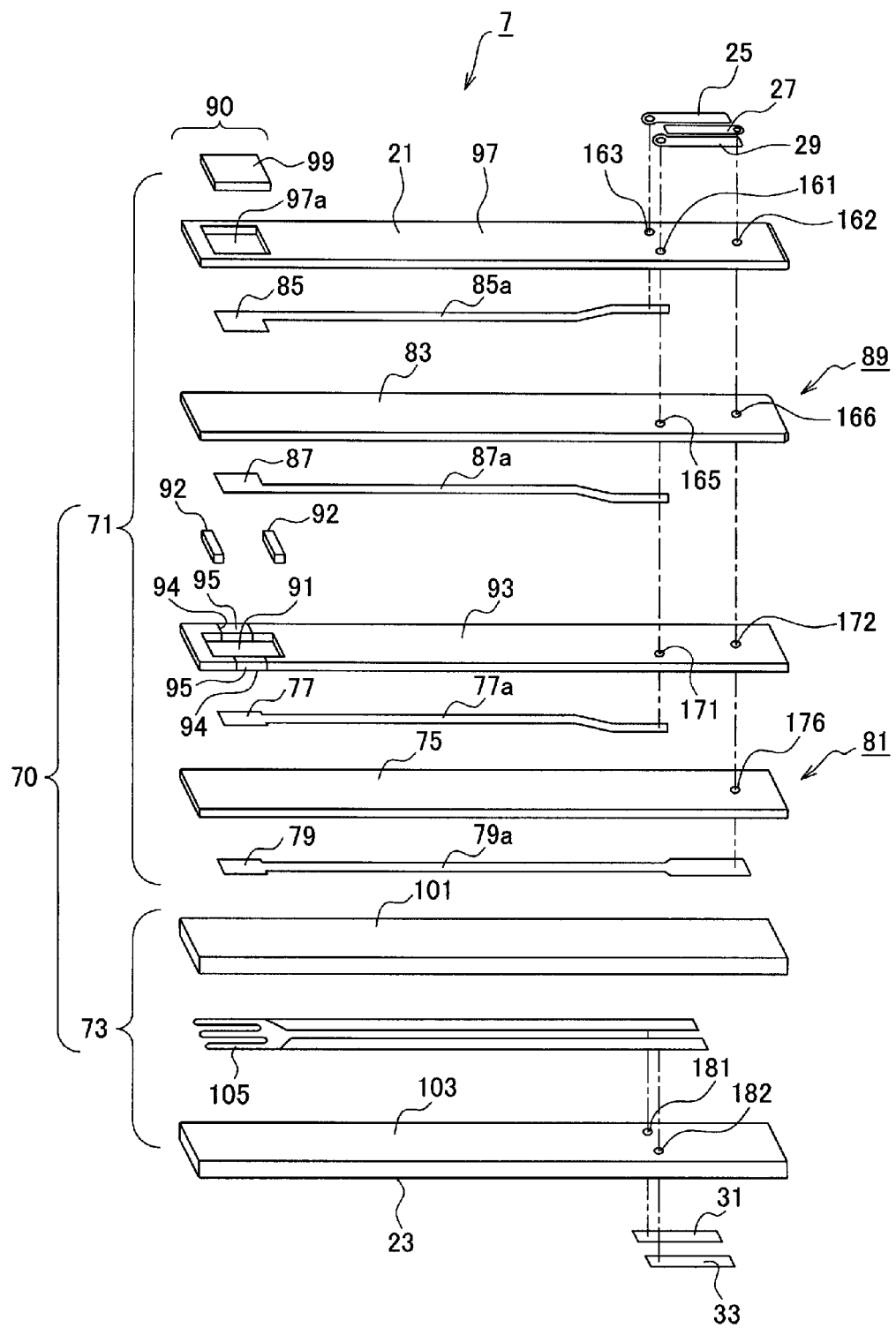
FIG. 3 is an exploded perspective view showing the gas sensor element.

FIG. 3 is an exploded perspective view showing the gas sensor element 7. FIG. 3 omits illustration of the protection layer 17 as well as a first long-side chamfer 121, a second long-side chamfer 122, a third long-side chamfer, and a fourth long-side chamfer, which will be described later.

As shown in FIG. 3 in an exploded condition, the element body 70 of the gas sensor element 7 includes the plate-shaped element 71 disposed on one side (upper side in FIG. 3) in a laminating direction and extending in the longitudinal direction, and the plate-shaped heater 73 disposed on a side (back side) opposite the element 71 and extending in the longitudinal direction.

The element 71 includes an oxygen concentration cell 81, an oxygen pump cell 89, an insulating spacer 93, and an insulating substrate 97.

The oxygen concentration cell 81 includes a solid electrolyte member 75, a porous electrode 77, a lead 77a, a porous electrode 79, and a lead 79a.

The solid electrolyte member 75 is a plate-shaped member formed primarily of zirconia. The pair of porous electrodes 77 and 79 are disposed on the front and back surfaces of the solid electrolyte member 75 so as to sandwich the solid electrolyte member 75.

One end of the lead 77a is connected to the porous electrode 77, and the lead 77a is disposed to extend in the longitudinal direction of the gas sensor element 7 (the element body 70) (in the left-right direction in FIG. 3). One end of the lead 79a is connected to the porous electrode 79, and the lead 79a is disposed to extend in the longitudinal direction of the gas sensor element 7 (the element body 70) (in the left-right direction in FIG. 3).

The oxygen pump cell 89 includes a solid electrolyte member 83, a porous electrode 85, a lead 85a, a porous electrode 87, and a lead 87a.

The solid electrolyte member 83 is a plate-shaped member formed primarily of zirconia. The pair of porous electrodes 85 and 87 are disposed on the front and back surfaces of the solid electrolyte member 83 so as to sandwich the solid electrolyte member 83.

One end of the lead 85a is connected to the porous electrode 85, and the lead 85a is disposed to extend in the longitudinal direction of the gas sensor element 7 (the element body 70) (in the left-right direction in FIG. 3). One end of the lead 87a is connected to the porous electrode 87, and the lead 87a is disposed to extend in the longitudinal direction of the gas sensor element 7 (the element body 70) (in the left-right direction in FIG. 3).

The solid electrolyte members 75 and 83 are formed of zirconia which contains yttria as a stabilizer in solid solution.

The porous electrodes 77, 79, 85, and 87 and the leads 77a, 79a, 85a, and 87a are formed primarily of Pt.

The insulating spacer 93 is a plate-shaped member formed primarily of alumina, and has a hollow gas measuring chamber 91. The insulating spacer 93 is interposed between the oxygen concentration cell 81 and the oxygen pump cell 89. As a result, the insulating spacer 93 forms at least a portion of the wall surface of the gas measuring chamber 91. The porous electrode 77 of the oxygen concentration cell 81 and the porous electrode 87 of the oxygen pump cell 89 are disposed in the gas measuring chamber 91 in such a manner as to be exposed to the gas measuring chamber 91.

Also, two porous members 92 are disposed within the gas measuring chamber 91. The porous members 92 are formed of, for example, alumina. The two porous members 92 are disposed such that they overlap with end portions of the porous electrode 87 and end portions of the porous electrode 77. Notably, the details of the porous members 92 will be described later.

The element 71 has two gas inlets 94 formed in respective sides thereof (sides of the insulating spacer 93). The gas inlets 94 serve as openings for introducing exhaust gas (gas to be measured) and communicate with the gas measuring chamber 91. Diffusion controlling portions 95 are formed in respective paths extending from the two gas inlets 94 to the gas measuring chamber 91. The diffusion controlling portions 95 are porous bodies formed of, for example, alumina and control diffusion of gas to be measured which flows into the gas measuring chamber 91. The diffusion controlling portions 95 are partially exposed to the outside from the gas inlets 94.

That is, in the gas sensor element 7, the gas inlets 94 are formed in the outermost surfaces of the element body 70 and face in two different directions, and the diffusion controlling portions 95 are exposed in the two different directions.

The insulating substrate 97 is a plate-shaped member formed primarily of alumina, and has an opening 97a which penetrates therethrough in the thickness direction. A ventilating portion 99 which is formed of a porous body similar to the case of the diffusion controlling portions 95 is disposed in the opening 97a. The ventilating portion 99 allows the porous electrode 85 of the oxygen pump cell 89 to be exposed to gas to be measured.

The gas measuring chamber 91 is located in a forward end region (left end region in FIG. 3) of the element body 70 (specifically, the element 71). With respect to the longitudinal direction of the element 71, a region where the gas measuring chamber 91 is formed, and a region located forward of the gas measuring chamber 91 constitute the detecting section 90 for detecting oxygen.

The heater 73 is formed such that a heat generating resistor pattern 105 formed primarily of Pt is sandwiched between insulating substrates 101 and 103 formed primarily of alumina.

The gas sensor element 7 has the three electrode pads 25, 27, and 29 formed on a rear end portion (right end portion in FIG. 3) of the first main surface 21, and the two electrode pads 31 and 33 formed on a rear end portion of the second main surface 23.

As shown in FIG. 3, the electrode pad 29 (right-hand electrode pad in FIG. 2) formed on the first main surface 21 is electrically connected to the porous electrode 77 of the oxygen concentration cell 81 through a through hole 161 provided in the insulating substrate 97, a through hole 165 provided in the solid electrolyte member 83, a through hole 171 provided in the insulating spacer 93, and the lead 77a. The electrode pad 29 is also electrically connected to the porous electrode 87 of the oxygen pump cell 89 through the through hole 161 provided in the insulating substrate 97, the through hole 165 provided in the solid electrolyte member 83, and the lead 87a. Thus, the porous electrode 77 and the porous electrode 87 are electrically connected to each other and thus have the same electrical potential.

Also, as shown in FIG. 3, another electrode pad (central electrode pad in FIG. 2) is electrically connected to the porous electrode 79 of the oxygen concentration cell 81 through a through hole 162 provided in the insulating substrate 97, a through hole 166 provided in the solid electrolyte member 83, a through hole 172 provided in the insulating spacer 93, a through hole 176 provided in the solid electrolyte member 75, and the lead 79a. Furthermore, as shown in FIG. 3, a further electrode pad 25 (left-hand electrode pad in FIG. 2) is electrically connected to the porous electrode 85 of the oxygen pump cell 89 through a through hole 163 provided in the insulating substrate 97 and the lead 85a.

Also, as shown in FIG. 3, the electrode pads 31 and 33 are electrically connected to respective opposite ends of the heat generating resistor pattern 105 through through-holes 181 and 182, respectively, provided in the insulating substrate 103.

Referring back to FIG. 2, since the thus-configured gas sensor element 7 is an elongated, substantially rectangular-parallelepiped plate element, it has four edges (longitudinal ridgelines) H1, H2, H3, and H4 extending its longitudinal direction (Y-axis direction in FIG. 2).

More specifically, the gas sensor element 7 has four outer walls extending its longitudinal direction; i.e., the first main surface 21 and the second main surface 23, and the first side surface 111 and the second side surface 113 in contact with the first main surface 21 and the second main surface 23. Also, the gas sensor element 7 has the first edge H1, which is a ridgeline between the first main surface 21 and the first side surface 111; the second edge H2, which is a ridgeline between the first main surface 21 and the second side surface 113; the third edge H3, which is a ridgeline between the second main surface 23 and the second side surface 113; and the fourth edge H4, which is a ridgeline between the second main surface 23 and the first side surface 111.

The first edge H1, the second edge H2, the third edge H3, and the fourth edge H4 are chamfered by 0.2 mm, thereby providing a first long-edge chamfer 121, a second long-edge chamfer 122, a third long-edge chamfer, and a fourth long-edge chamfer. In FIG. 2, since the third long-edge chamfer and the fourth long-edge chamfer are invisible, the illustration of the third and fourth long-edge chamfers with reference numerals is omitted.

The gas sensor element 7 is also chamfered at four ridgelines of its rear end surface 129 (upper end surface in FIG. 2), thereby forming rear end chamfers 131 while leaving the central rear end surface 129 (perpendicular to the longitudinal direction).

The protection layer 17 is formed of porous alumina and covers at least the detecting section 90 of the element body 70.

1-3. Internal Structure of Forward End Portion of Gas Sensor Element

Next, the internal structure of a forward end portion of the gas sensor element 7 will be described.

Figure 4:
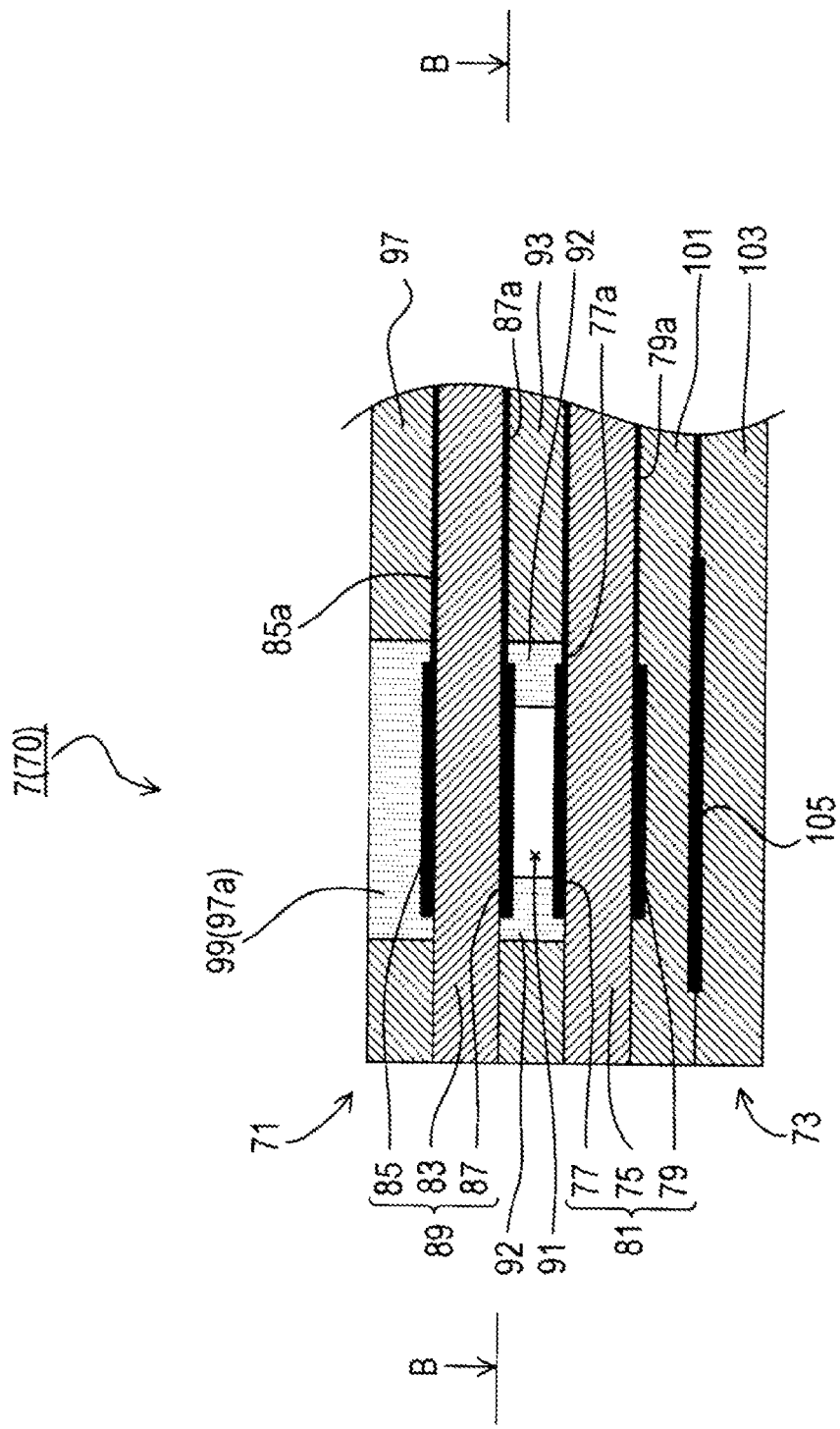
FIG. 4 is a sectional view of the gas sensor element taken along line A-A of FIG. 2.

FIG. 4 is a sectional view of the gas sensor element 7 taken along line A-A of FIG. 2 and showing the internal structure of the forward end portion of the gas sensor element 7. Notably, in FIG. 4, the protection layer 17 is omitted.

As shown in FIG. 4, the gas sensor element 7 includes two cells (the oxygen concentration cell 81 and the oxygen pump cell 89), and these two cells are stacked or layered with the insulating spacer 93 interposed therebetween.

The oxygen concentration cell 81 has a structure in which a pair of electrodes; i.e., the porous electrode 77 and the porous electrode 79, are disposed on the front and back surfaces of the solid electrolyte member 75, respectively. The oxygen pump cell 89 has a structure in which a pair of electrodes; i.e., the porous electrode 85 and the porous electrode 87, are disposed on the front and back surfaces of the solid electrolyte member 83.

The gas measuring chamber 91 is a cavity whose upper wall is formed by the oxygen concentration cell 81, whose lower wall is formed by the oxygen pump cell 89, and whose peripheral wall is formed by the insulating spacer 93.

The porous electrode 77 of the oxygen concentration cell 81 and the porous electrode 87 of the oxygen pump cell 89 are disposed in the gas measuring chamber 91 in such a manner as to be exposed to the gas measuring chamber 91.

Also, the two porous members 92 are disposed in the gas measuring chamber 91. The porous members 92 are composed of porous bodies formed of, for example, ceramic such as alumina. The two porous members 92 are disposed such that they overlap with forward and rear ends of the porous electrode 87 in the longitudinal direction. Also, the two porous members 92 are disposed such that they overlap with forward and rear ends of the porous electrode 77 in the longitudinal direction. Namely, each porous member 92 partially covers the porous electrode 77, and extends from a position on the porous electrode 77, beyond the corresponding end of the porous electrode 77, to a position on a surface of the solid electrolyte member 75, which surface is exposed to the gas measuring chamber 91.

Figure 5:
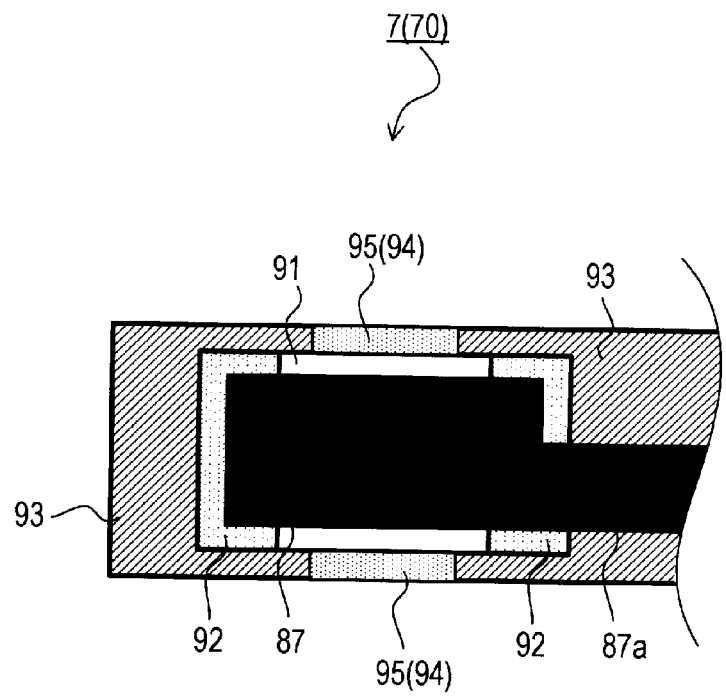
FIG. 5 is a sectional view of the gas sensor element taken along line B-B of FIG. 4.

FIG. 5 shows a sectional view of the gas sensor element 7 taken along line B-B of FIG. 4.

As shown in FIGS. 5 and 4, the two porous members 92 are disposed at the forward end (left-hand end in FIG. 5) and the rear end (right-hand end in FIG. 5), respectively, of the gas measuring chamber 91 formed in the insulating spacer 93.

Also, the two porous members 92 are disposed such that they overlap with the forward end (left-hand end in FIG. 5) and the rear end (right-hand end in FIG. 5) of the porous electrode 87 in the longitudinal direction. Namely, as shown in FIG. 4, each porous member 92 is disposed in the gas measuring chamber 91 so as to sandwich at least a part of the corresponding end portion of the porous electrode 87 in cooperation with the solid electrolyte member 83.

In the porous electrode 87 having the above-described configuration, movement (movement due to shrinkage) of a portion sandwiched between the porous member 92 and the solid electrolyte member 83 is restrained. Therefore, it is possible to restrain shrinkage of the porous electrode 87 at the time of manufacture of the gas sensor element 7, which shrinkage would otherwise occur at the time of heating in a debindering step or at the beginning of a firing step. Thus, occurrence of green breakage in the solid electrolyte member 83 can be prevented.

Also, since the end portions of the porous electrode 87 are sandwiched between the solid electrolyte member 83 and the porous members 92, the end portions of the porous electrode 87 can receive oxygen through the porous members 92, unlike a structure in which end portions of a porous electrode are sandwiched between a dense member and a solid electrolyte member.

Similarly, the two porous members 92 are disposed such that they overlap with the forward and rear ends of the porous electrode 77. Namely, each porous member 92 is disposed in the gas measuring chamber 91 so as to sandwich at least a part of the corresponding end portion of the porous electrode 77 in cooperation with the solid electrolyte member 75 (see FIG. 4).

Therefore, as in the case of the porous electrode 87, in the porous electrode 77 as well, movement (movement due to shrinkage) of a portion sandwiched between the porous member 92 and the solid electrolyte member 75 is restrained. Therefore, shrinkage of the porous electrode 77 can be restrained, and occurrence of green breakage in the solid electrolyte member 75 can be prevented. Also, as in the case of the porous electrode 87, the porous electrode 77 can receive oxygen through the porous members 92.

Also, as shown in FIGS. 4 and 5, the porous electrode 87 and the porous electrode 77 are formed to be smaller than the cross sectional area of the gas measuring chamber 91, and are disposed in a state in which they are spaced from the insulating spacer 93.

Since there does not exist a region where the porous electrode 87 is in contact with the insulating spacer 93, it is possible to prevent generation of stress in the solid electrolyte member 83, which stress would otherwise be generated due to the difference in shrinkage amount between the porous electrode 87 and the insulating spacer 93.

In the case of the porous electrode 77 as well, there does not exist a region where the porous electrode 77 is in contact with the insulating spacer 93. Therefore, it is possible prevent generation of stress in the solid electrolyte member 75, which stress would otherwise be generated due to the difference in shrinkage amount between the porous electrode 77 and the insulating spacer 93.

In the case where the diffusion resistance of the diffusion controlling portions 95 provided in the gas inlets 94 is assumed to be 1.0, the diffusion resistance of each of the two porous members 92 is set to 0.1 to 1.0, and the diffusion resistance of each of the porous electrode 87 and the porous electrode 77 is set to 1.0 to about 100.

Namely, in the gas sensor element 7, the diffusion resistance of the porous members 92 is equal to or smaller than the diffusion resistance of the diffusion controlling portions 95.

In the configuration in which the diffusion resistance of the porous members 92 is equal to or smaller than the diffusion resistance of the diffusion controlling portions 95 as described above, diffusion of a particular gas (for example, oxygen) is not controlled or limited in the porous members 92. As a result, the amount of the particular gas (for example, oxygen) supplied through the porous members 92 can be made sufficiently large, and blackening of the solid electrolyte member 83 and the solid electrolyte member 75 can be prevented to a greater degree.

Also, in the gas sensor element 7, the diffusion resistance of the porous electrode 87 is equal to or larger than the diffusion resistance of the diffusion controlling portions 95.

In the configuration in which the diffusion resistance of the porous electrode 87 is equal to or larger than the diffusion resistance of the diffusion controlling portions 95 as described above, diffusion of the particular gas (for example, oxygen) in the porous electrode 87 can be controlled or limited, whereby pumping of the particular gas (for example, oxygen) by the porous electrode 87 can be properly realized. As a result, the accuracy in detecting the particular gas (for example, oxygen) by the gas sensor element 7 can be increased.

In the case of the porous electrode 77 as well, its diffusion resistance is equal to or larger than the diffusion resistance of the diffusion controlling portions 95 as in the case of the porous electrode 87. Therefore, diffusion of the particular gas (for example, oxygen) in the porous electrode 77 can be controlled or limited, whereby pumping of the particular gas (for example, oxygen) by the porous electrode 77 can be properly realized.

1-4. Method of Manufacturing Gas Sensor

A method of manufacturing the air/fuel ratio sensor 1 of the present embodiment will be described with reference to FIGS. 6 and 7.

Figure 6:
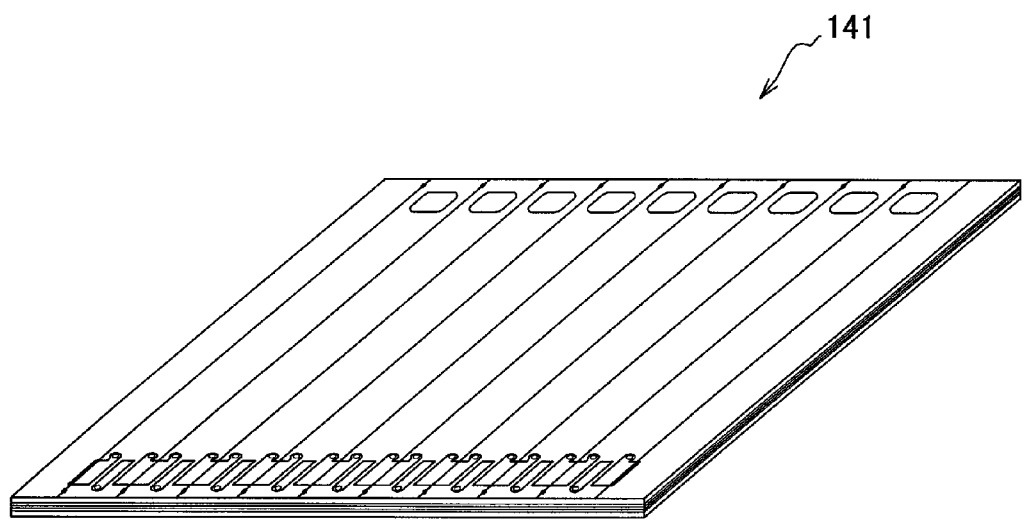
FIG. 6 is an explanatory view regarding a method of manufacturing a green compact of the gas sensor elements.

FIG. 6 is an explanatory view regarding a method of manufacturing a green compact 141 of the gas sensor elements. FIG. 7 is an explanatory view showing the gas sensor element in the middle of manufacture.

In manufacture of the gas sensor element 7, first, an uncompressed laminate is prepared by laminating together publicly known various materials used to form the gas sensor element 7; specifically, green solid electrolyte sheets used to form the solid electrolyte members 75 and 83 of the element 71, green insulating sheets used to form the insulating substrate 97 of the element 71, green insulating sheets used to form the insulating substrates 101 and 103 of the heater 73, among others. The uncompressed laminate has green electrode pads which are to become the electrode pads 25, 27, 29, 31, and 33, among others, formed beforehand therein.

Among these materials, for example, the green solid electrolyte sheet is formed in the following manner. First, alumina powder, butyral resin, etc., are added to ceramic powder which predominantly contains zirconia. Into the resultant mixture, a mixed solvent (toluene and methyl ethyl ketone) is mixed, thereby forming slurry. The slurry is formed into a sheet by a doctor blade process, and the mixed solvent is volatilized, thereby yielding the green solid electrolyte sheet.

The green insulating sheet is formed in the following manner. First, butyral resin and dibutyl phthalate are added to ceramic powder which predominantly contains alumina. Into the resultant mixture, a mixed solvent (toluene and methyl ethyl ketone) is mixed, thereby forming slurry. The slurry is formed into a sheet by the doctor blade process, and the mixed solvent is volatilized, thereby yielding the green insulating sheet.

Green diffusion controlling portions are formed in the following manner. First, alumina powder, a pore-forming agent (carbon powder or the like), and a plasticizer are wet-mixed, thereby forming slurry in which the alumina powder, the pore-forming agent, and the plasticizer are dispersed. The plasticizer contains butyral resin and DBP. The slurry is applied to regions where the diffusion controlling portions 95 and the ventilating portion 99 are to be formed through firing, thereby forming the green diffusion controlling portions.

Green porous members are formed in the following manner. First, alumina powder, a pore-forming agent (carbon powder or the like), and a binder are wet-mixed, thereby forming paste in which the alumina powder, the pore-forming agent, and the binder are dispersed. Butyral resin is used as the binder. The paste is applied to regions where the porous members 92 are to be formed through firing, thereby forming the green porous members.

At that time, the diffusion resistances of the diffusion controlling portions 95, the ventilating portion 99, and the porous members 92 obtained through firing can be freely adjusted by adjusting the amount of the binder in the paste, the compositional ratio of solid contents, the amount of the pore-forming agent added, etc.

Green porous electrodes and green leads are formed as follows. First, platinum, partially stabilized zirconia, and a binder are wet-mixed, thereby forming paste in which platinum, partially stabilized zirconia, and the binder are dispersed. The paste is applied to regions where the porous electrodes and the leads are to be formed through firing, thereby forming the green porous electrodes and the green leads. At that time, the diffusion resistances of the porous electrodes and the leads obtained through firing can be freely adjusted by adjusting the amount of the binder, the compositional ratio of solid contents, the amount of the pore-forming agent added, etc.

Then, the uncompressed laminate is compressed under a pressure of 1 MPa, thereby yielding the green compact 141 as shown in FIG. 6. A method of manufacturing the uncompressed laminate is similar to a publicly known method of manufacturing a gas sensor element; therefore, detailed description of the method is omitted.

The green compact 141 yielded through application of pressure is cut into a plurality of (e.g., ten) green laminates, each having a predetermined size substantially identical to that of the element 71 and the heater 73 of the gas sensor element 7.

Figure 7:
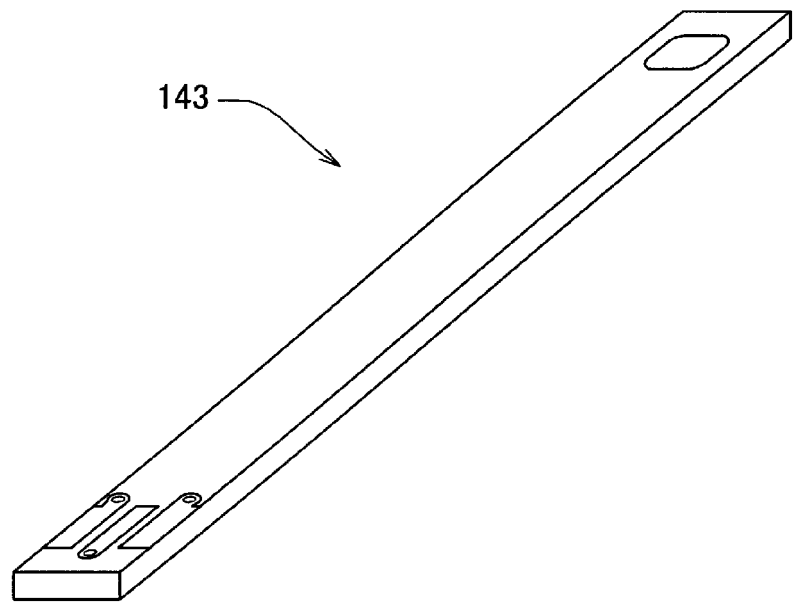
FIG. 7 is an explanatory view showing the gas sensor element in the middle of manufacture.

Subsequently, the green laminate is debindered (debindering step) and is, furthermore, subjected to regular firing at 1,500° C. for one hour (firing step), thereby yielding a fired laminate 143 as shown in FIG. 7.

Next, the fired laminate 143 is chamfered at its longitudinally extending four edges (the first edge H1, the second edge H2, the third edge H3, and the fourth edge H4), thereby forming the first long-edge chamfer 121, the second long-edge chamfer 122, the third long-edge chamfer, and the fourth long-edge chamfer (see FIG. 2). Specifically, the longitudinally extending four edges (the first edge H1, the second edge H2, the third edge H3, and the fourth edge H4) of the fired laminate 143 are applied to a grindstone for well-known chamfering. Thus, the element body 70 is yielded.

After the element body 70 is yielded as mentioned above, a green protection layer is formed around a forward end portion of the element body 70. The green protection layer becomes the protection layer 17 (see FIG. 2) through firing.

After that, the green protection layer is subjected to heat treatment. Specifically, the element body 70 having the green protection layer formed thereon is subjected to heat treatment at a temperature of 1,000° C. for three hours, thereby yielding the gas sensor element 7 on which the protection layer 17 is formed.

The thus-formed gas sensor element 7 is assembled to the metallic shell 5 in a subassembling step.

Specifically, in this subassembling step, the gas sensor element 7 manufactured by the above method is inserted into the metallic holder 51; furthermore, the gas sensor element 7 is fixed in place by the ceramic holder 41 and the talc ring 43, thereby forming a subassembly. Subsequently, while the subassembly is fixed to the metallic shell 5, and an axially rear end portion of the gas sensor element 7 is inserted through the talc ring 45 and the ceramic sleeve 9, these members are inserted into the metallic shell 5.

Then, the rear end portion 47 of the metallic shell 5 is crimped to press and hold the ceramic sleeve 9, thereby yielding a lower subassembly. The protector 55 is attached beforehand to the lower subassembly.

Meanwhile, the outer tube 57, the separator 13, the grommet 61, etc., are assembled together, thereby yielding an upper subassembly. Then, the lower subassembly and the upper subassembly are joined together, thereby yielding the air/fuel ratio sensor 1.

1-5. Effects

As described above, the gas sensor element 7 of the air/fuel ratio sensor 1 according to the present embodiment is configured such that at least a part of each end portion of the porous electrode 87 is sandwiched between the porous member 92 and the solid electrolyte member 83. Therefore, movement (movement due to shrinkage) of portions of the porous electrode 87 sandwiched between the porous members 92 and the solid electrolyte member 83 is restrained.

Therefore, it is possible to restrain shrinkage of the porous electrode 87 at the time of manufacture of the gas sensor element 7, which shrinkage would otherwise occur at the time of heating in a debindering step or at the beginning of a firing step. Thus, occurrence of green breakage in the solid electrolyte member 83 can be prevented. Accordingly, it is possible to prevent a crack due to green breakage from being generated in the solid electrolyte member 83 obtained through firing.

Also, since the end portions of the porous electrode 87 are sandwiched between the solid electrolyte member 83 and the porous members 92, the end portions of the porous electrode 87 can receive oxygen through the porous members 92, unlike a structure in which end portions of a porous electrode are sandwiched between a dense member and a solid electrolyte member. Therefore, shortage of oxygen is unlikely to occur, and blackening of the solid electrolyte member 83 can be prevented.

Notably, the two porous members 92 are disposed such that they overlap with the forward and rear ends of the porous electrode 77 in addition to the forward and rear ends of the porous electrode 87. Namely, each porous member 92 is disposed in the gas measuring chamber 91 so as to sandwich at least a part of the corresponding end portion of the porous electrode 77 in cooperation with the solid electrolyte member 75 (see FIG. 4).

Therefore, as in the case of the porous electrode 87, in the porous electrode 77 as well, movement (movement due to shrinkage) of portions sandwiched between the porous members 92 and the solid electrolyte member 75 is restrained. Therefore, shrinkage of the porous electrode 77 can be restrained, and occurrence of green breakage in the solid electrolyte member 75 can be prevented. Thus, it is possible to prevent a crack due to green breakage from being generated in the solid electrolyte member 83 obtained through firing.

Notably, as in the case of the porous electrode 87, the porous electrode 77 can receive oxygen through the porous members 92. Therefore, shortage of oxygen is unlikely to occur, and blackening of the solid electrolyte member 83 can be prevented.

The porous electrode 87 is formed to be smaller than the cross sectional area of the gas measuring chamber 91, and is disposed in a state in which it is spaced from the insulating spacer 93. Since there does not exist a region where the porous electrode 87 is in contact with the insulating spacer 93, it is possible prevent generation of stress in the solid electrolyte member 83, which stress would otherwise be generated due to the difference in shrinkage amount between the porous electrode 87 and the insulating spacer 93.

Therefore, it is possible to prevent occurrence of "green breakage" in the solid electrolyte member 83, which would otherwise occur due to the difference in shrinkage amount between the porous electrode 87 and the insulating spacer 93, to thereby prevent a crack due to the green breakage from being generated in the solid electrolyte member 83 obtained through firing.

Notably, as in the case of the porous electrode 77 as well, there does not exist a region where the porous electrode 77 is in contact with the insulating spacer 93. Therefore, it is possible to prevent occurrence of "green breakage" in the solid electrolyte member 75, which would otherwise occur due to the difference in shrinkage amount between the porous electrode 77 and the insulating spacer 93, to thereby prevent a crack due to the green breakage from being generated in the solid electrolyte member 75 obtained through firing.

Therefore, the gas sensor element 7 can prevent blackening of the solid electrolyte member 83 and the solid electrolyte member 75, and can prevent green breakage of the solid electrolyte member 83 and the solid electrolyte member 75 during manufacture to thereby prevent cracking of the solid electrolyte member 83 and the solid electrolyte member 75 produced through firing.

In the gas sensor element 7, the diffusion resistance of the porous members 92 is equal to or smaller than the diffusion resistance of the diffusion controlling portion 95. In the configuration in which the diffusion resistance of the porous members 92 is equal to or smaller than the diffusion resistance of the diffusion controlling portion 95 as described above, diffusion of a particular gas (for example, oxygen) is not controlled or limited in the porous members 92. As a result, the amount of the particular gas (for example, oxygen) supplied through the porous members 92 can be made sufficiently large, and blackening of the solid electrolyte member 83 and the solid electrolyte member 75 can be prevented to a greater degree.

Also, in the gas sensor element 7, the diffusion resistance of the porous electrode 87 is larger than the diffusion resistance of the diffusion controlling portion 95. In the configuration in which the diffusion resistance of the porous electrode 87 is larger than the diffusion resistance of the diffusion controlling portions 95 as described above, diffusion of the particular gas (for example, oxygen) in the porous electrode 87 can be controlled or limited, whereby pumping of the particular gas (for example, oxygen) by the porous electrode 87 can be properly realized. As a result, the accuracy in detecting the particular gas (for example, oxygen) by the gas sensor element 7 can be increased.

In the case of the porous electrode 77 as well, its diffusion resistance is larger than the diffusion resistance of the diffusion controlling portions 95 as in the case of the porous electrode 87. Therefore, diffusion of the particular gas (for example, oxygen) in the porous electrode 77 can be controlled or limited, whereby pumping of the particular gas (for example, oxygen) by the porous electrode 77 can be properly realized.

1-6. Correspondence Between Claims and Present Embodiment

Correspondence in wording between claims and the present embodiment will be described below.

The porous electrode 77 and the porous electrode 79 correspond to the pair of electrodes; the porous electrode 85 and the porous electrode 87 correspond to the pair of electrodes; the insulating spacer 93 corresponds to the dense member; and the gas measuring chamber 91 corresponds to the hollow cavity and the measuring chamber.

The porous electrode 77 and the porous electrode 87 correspond to the cavity side electrode; and the diffusion controlling portions 95 correspond to the diffusion resistance portion.

2. Second Embodiment

An oxygen sensor having a second gas sensor element 107 in which a porous member is disposed to surround the entire circumferences of porous electrodes will be described as a second embodiment.

The oxygen sensor of the second embodiment is constructed by replacing the gas sensor element 7 of the air/fuel ratio sensor 1 of the first embodiment with a second gas sensor element 107, changing the number of the connection terminals 15 and the number of the lead wires 35, and changing the shapes of the separator 13, the grommet 61, etc.

Figure 8:
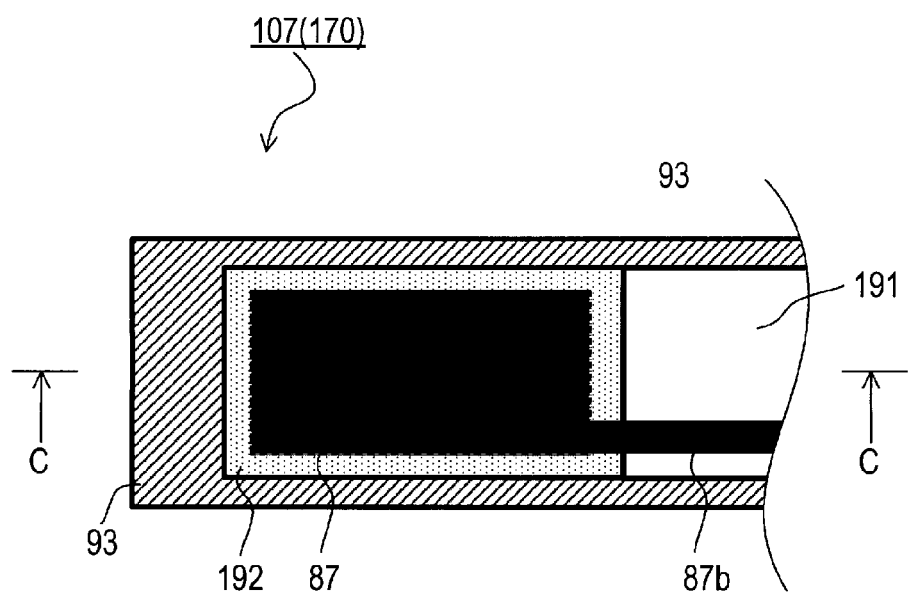
FIG. 8 is a sectional view showing the internal structure of a second gas sensor element.
Figure 9:
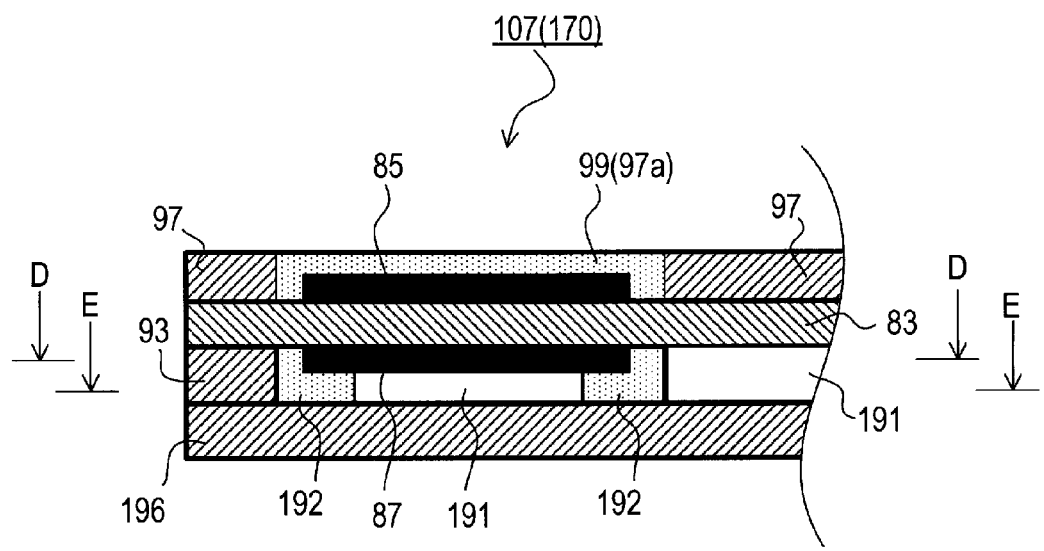
FIG. 9 is a sectional view of the second gas sensor element taken along line C-C of FIG. 8.
Figure 10:
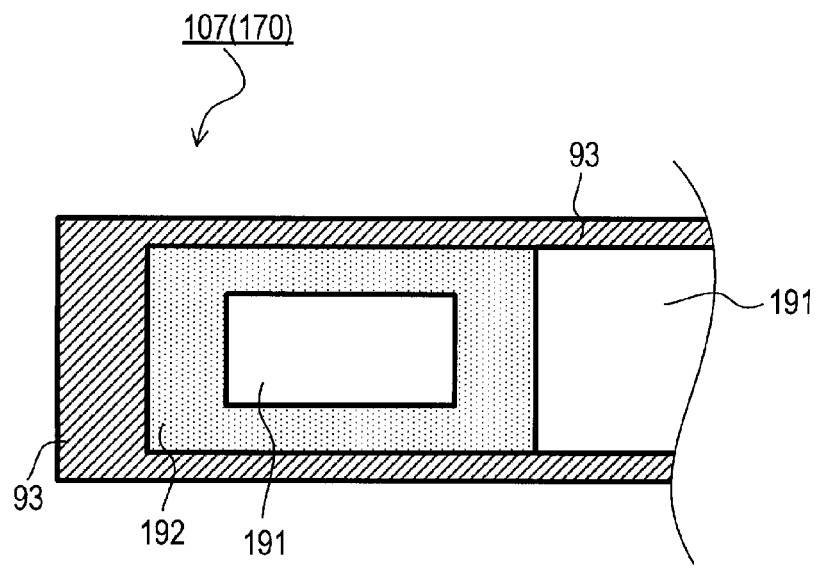
FIG. 10 is a sectional view of the second gas sensor element taken along line E-E of FIG. 9.

As shown in FIGS. 8, 9, and 10, the second gas sensor element 107 has a second porous member 192 which is disposed in an atmospheric chamber 191 of the second element body 170 such that it surrounds the entire circumference of the porous electrode 87. The second porous member 192 includes at least two sections which are arranged on or at opposite sides of the atmospheric chamber 191. In the embodiment shown in FIGS. 8, 9, and 10, the second porous member 192 includes four sections each arranged on or at a side of the atmospheric chamber 191 to form a ring-like second porous member 192. The sections are connected with each other.

FIG. 8 is a sectional view showing the internal structure of the second gas sensor element 107, and corresponds to a sectional view of the second gas sensor element 107 taken along line D-D of FIG. 9. FIG. 9 is a sectional view of the second gas sensor element 107 taken along line C-C of FIG. 8. FIG. 10 is a sectional view of the second gas sensor element 107 taken along line E-E of FIG. 9.

The second gas sensor element 107 including such a second porous member 192 has a structure in which the entirety of a peripheral edge portion of the porous electrode 87 is sandwiched between the second porous member 192 and the solid electrolyte member 83.

Notably, the second gas sensor element 107 does not have a two-cell structure (including the oxygen concentration cell 81 and the oxygen pump cell 89) employed in the above-described gas sensor element 7, but has a one-cell structure (an oxygen pump cell having the solid electrolyte member 83, the porous electrode 85, and the porous electrode 87). The atmospheric chamber 191 of the second gas sensor element 107 is formed by the solid electrolyte member 83, the insulating spacer 93, and the insulating substrate 196. The atmospheric chamber 191 is a formed as a cavity which is open at the rear end of the second gas sensor element 107, and is configured to introduce the atmosphere through the opening at the rear end. In the second gas sensor element 107, a second lead 87b connected to the porous electrode 87 is formed to have a smaller width as compared with the lead 87a of the above-described gas sensor element 7.

The second gas sensor element 107 having such a one-cell structure is disposed such that the porous electrode 85 comes into contact with gas to be measured in a state in which the atmosphere (reference gas) is introduced into the atmospheric chamber 191. Thus, an electromotive force is produced between the porous electrode 85 and the porous electrode 87. This electromotive force changes with the ratio between the oxygen concentration (concentration of a particular gas) in the gas to be measured and the oxygen concentration in the atmosphere. Therefore, oxygen contained in the gas to be measured can be detected through use of the electromotive force produced between the porous electrode 85 and the porous electrode 87 of the second gas sensor element 107.

Notably, components of the second gas sensor element 107 which have the same configurations as those of the gas sensor element 7 are denoted by the same reference numerals.

Like the above-described as sensor element 7, this second gas sensor element 107 can prevent blackening of the solid electrolyte member 83, and can prevent green breakage of the solid electrolyte member 83 during manufacture to thereby prevent cracking of the solid electrolyte member 83 produced through firing.

Namely, the structure of the gas sensor element is not limited to the structure in which porous members are disposed at the forward and rear ends of a porous electrode in the longitudinal direction (the gas sensor element 7), and there can be employed the structure in which a porous member is disposed over the entire circumference of a porous electrode (the second gas sensor element 107).

Correspondence in wording between claims and the present embodiment will be described below.

The porous electrode 85 and the porous electrode 87 correspond to the pair of electrodes; the insulating spacer 93 and the insulating substrate 196 correspond to the dense member; and the atmospheric chamber 191 corresponds to the hollow cavity and the atmospheric chamber. The second porous member 192 corresponds to the porous member; the porous electrode 87 corresponds to the cavity side electrode; and the diffusion controlling portion 95 corresponds to the diffusion resistance portion.

3. Third Embodiment

An oxygen sensor including a third gas sensor 207 which has a single gas introduction passage extending from an outer wall surface to a hollow cavity (gas measuring chamber) will be described as a third embodiment.

The oxygen sensor of the third embodiment is constructed by replacing the gas sensor element 7 of the air/fuel ratio sensor 1 of the first embodiment with a third gas sensor element 207.

Figure 11:
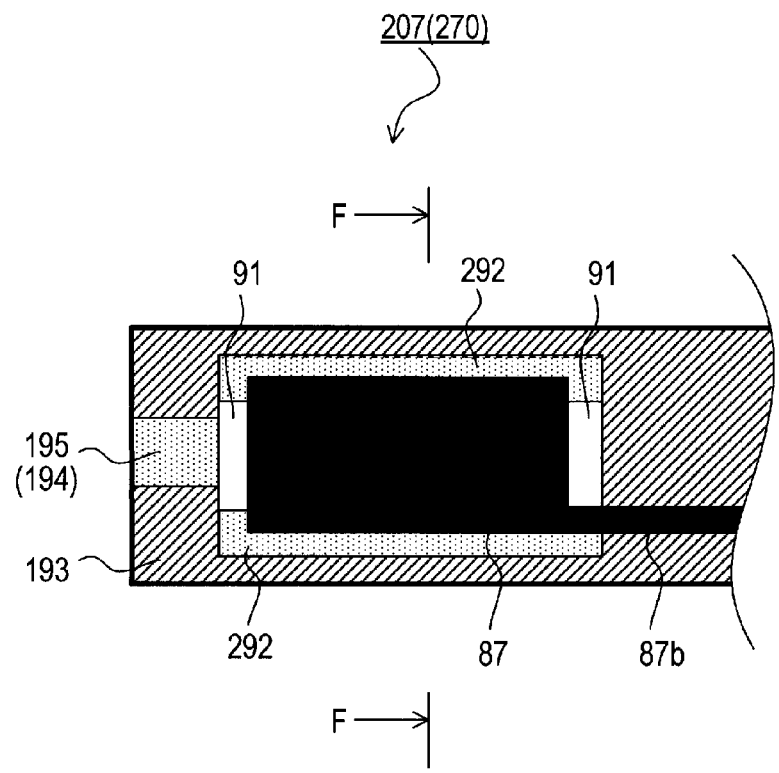
FIG. 11 is a sectional view showing the internal structure of a third gas sensor element.
Figure 12:
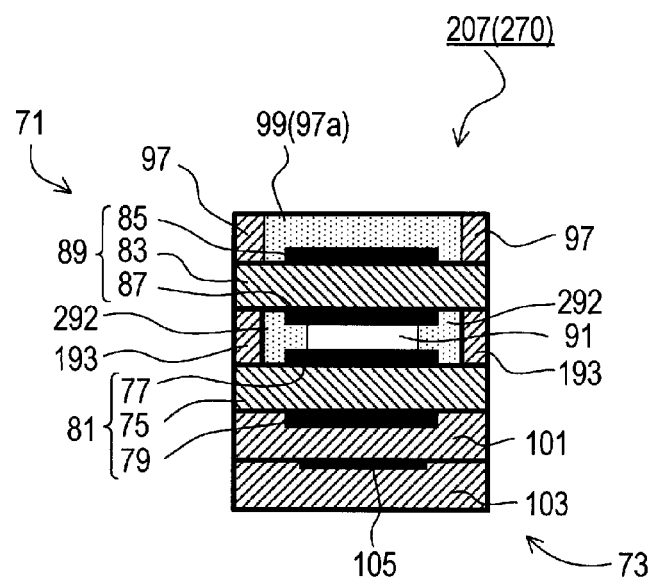
FIG. 12 is a sectional view of the third gas sensor element taken along line F-F of FIG. 11.

As shown in FIGS. 11 and 12, the third gas sensor element 207 has a single second gas inlet 194 extending from an outer end surface to the gas measuring chamber 91. Notably, the second gas inlet 194 is not provided in the side surface of the third element body 270, but is provided at the forward end (the left end in FIG. 11) of the third element body 270. A second diffusion controlling portion 195 constituted by a porous body formed of alumina or the like is disposed in the second gas inlet 194.

FIG. 11 is a sectional view showing the internal structure of the third gas sensor element 207. FIG. 12 is a sectional view of the third gas sensor 207 taken along line F-F of FIG. 11.

The third gas sensor element 207 has two third porous members 292 which are disposed in the gas measuring chamber 91 of the third element body 270 such that the third porous members 292 are located at the opposite ends (the left and right ends in FIG. 12) of the porous electrode 87 in the width direction orthogonal to the longitudinal direction. The two third porous members 292 can be spaced from each other in this embodiment.

The third gas sensor element 207 having the two third porous members 292 is configured such that the end portions of the porous electrode 87 are sandwiched between the two third porous members 292 and the solid electrolyte member 83. Also, the third gas sensor element 207 is configured such that the end portions of the porous electrode 77 are sandwiched between the two third porous members 292 and the solid electrolyte member 75.

Notably, the third gas sensor element 207 has a two-cell structure (including the oxygen concentration cell 81 and the oxygen pump cell 89) like the above-described gas sensor element 7. The gas measuring chamber 91 of the third gas sensor element 207 is formed by the solid electrolyte member 83, the second insulating spacer 193, and the solid electrolyte member 75. Notably, components of the third gas sensor element 207 which have the same configurations as those of the above-described gas sensor element are denoted by the same reference numerals.

Like the above-described as sensor element 7, this third gas sensor element 207 can prevent blackening of the solid electrolyte member 83 and the solid electrolyte member 75, and can prevent green breakage of the solid electrolyte member 83 and the solid electrolyte member 75 during manufacture, to thereby prevent cracking of the solid electrolyte member 83 and the solid electrolyte member 75 produced through firing.

Namely, the structure of the gas sensor element is not limited to the structure in which a plurality of gas introduction passages each extending from an outer wall surface to the hollow cavity (gas measuring chamber) are provided (the gas sensor element 7), and there can be employed the structure in which a single gas introduction passage is provided (the third gas sensor element 207).

Correspondence in wording between claims and the present embodiment will be described below.

The porous electrode 77 and the porous electrode 79 correspond to the pair of electrodes; the porous electrode 85 and the porous electrode 87 correspond to the pair of electrodes; the second insulating spacer 193 corresponds to the dense member; and the gas measuring chamber 91 corresponds to the hollow cavity and the measuring chamber. The third porous members 292 correspond to the porous ember; the porous electrode 77 and the porous electrode 87 correspond to the cavity side electrode; and the second diffusion controlling portion 195 corresponds to the diffusion resistance portion.

4. Fourth Embodiment

An oxygen sensor including a fourth gas sensor 307 in which a porous member is provided along three edges of a porous electrode, the edges corresponding to three sides of the four sides of the porous electrode, will be described as a fourth embodiment.

The oxygen sensor of the fourth embodiment is constructed by replacing the gas sensor element 7 of the air/fuel ratio sensor 1 of the first embodiment with a fourth gas sensor element 307.

Figure 13:
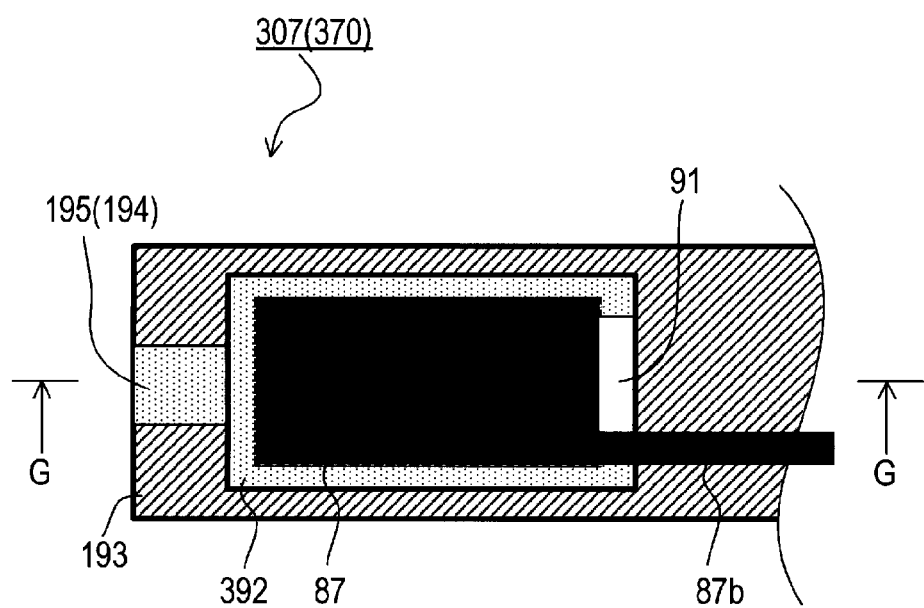
FIG. 13 is a sectional view showing the internal structure of a fourth gas sensor element.
Figure 14:
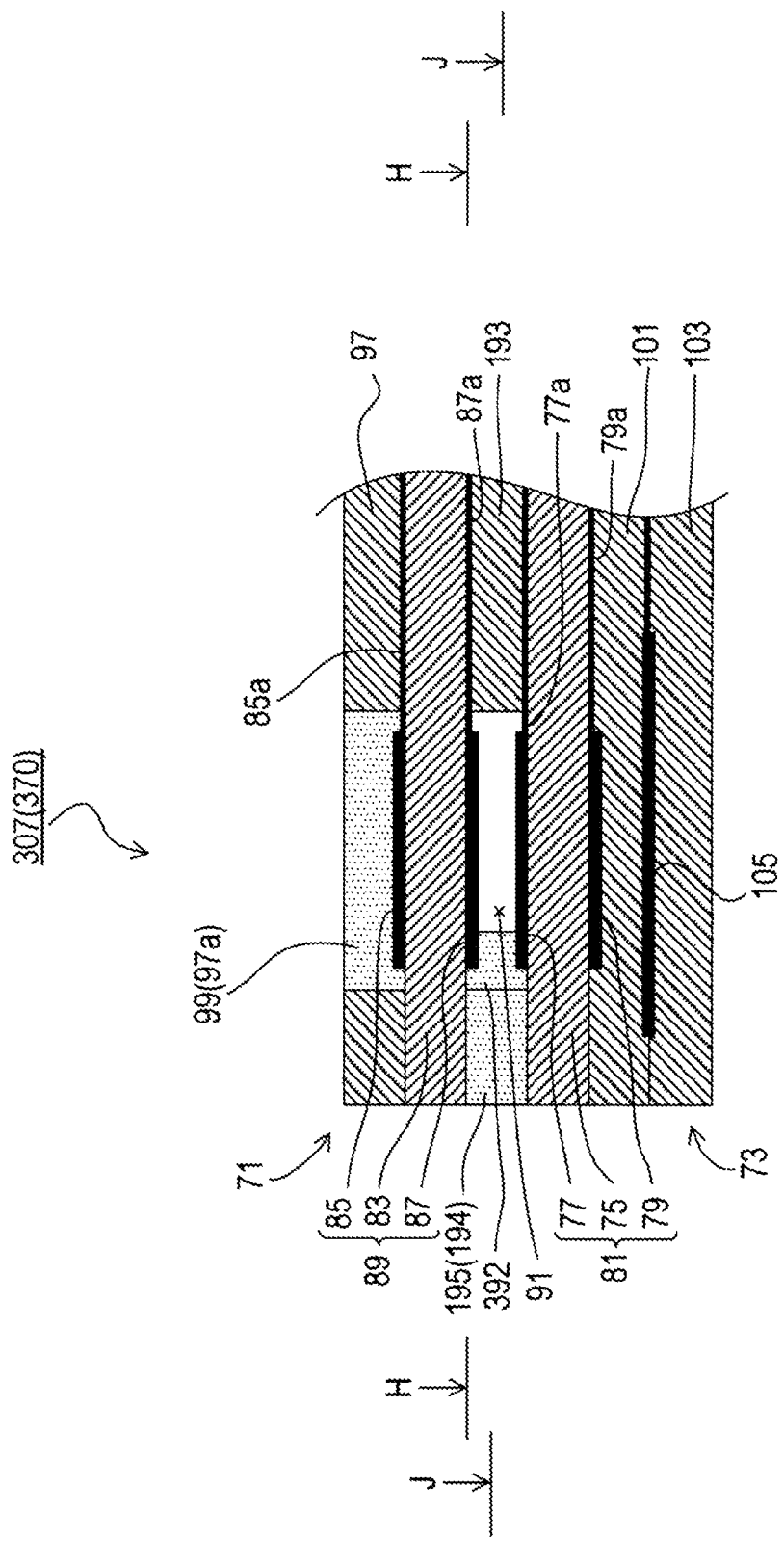
FIG. 14 is a sectional view of the fourth gas sensor element taken along line G-G of FIG. 13.
Figure 15:
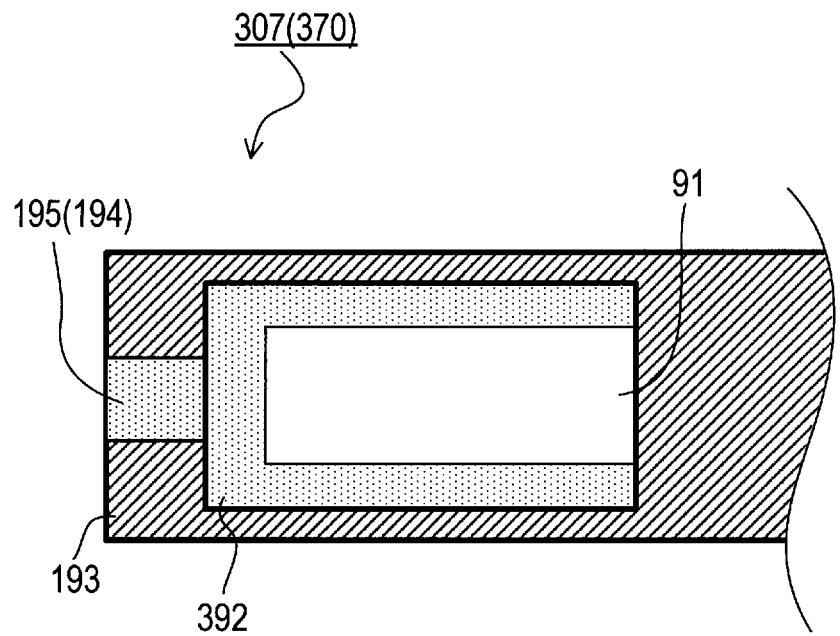
FIG. 15 is a sectional view of the fourth gas sensor element taken along line J-J of FIG. 14.

As shown in FIGS. 13, 14, and 15, the fourth gas sensor element 307 has a fourth porous member 392 which is provided in the gas measuring chamber 91 of the fourth element body 370 such that the fourth porous member 392 extends along three edges of the porous electrode 87, which edges correspond to three sides of the four sides of the porous electrode. The fourth porous member 392 includes at least two sections which are arranged at opposite sides of the gas measuring chamber 91. The two sections are connected by a third section to form an U-shaped fourth porous member 392.

FIG. 13 is a sectional view showing the internal structure of the fourth gas sensor element 307, and corresponds to a sectional view of the fourth gas sensor element 307 taken along line H-H of FIG. 14. FIG. 14 is a sectional view of the fourth gas sensor element 307 taken along line G-G of FIG. 13. FIG. 15 is a sectional view of the fourth gas sensor element 307 taken along line J-J of FIG. 14.

The fourth gas sensor element 307 having the fourth porous member 392 is configured such that the three edges of the porous electrode 87 corresponding to three sides of the four sides thereof are sandwiched between the fourth porous member 392 and the solid electrolyte member 83, particularly between the three sections of the fourth porous member 392 and the solid electrolyte member 83. Also, the fourth gas sensor element 307 is configured such that three edges of the porous electrode 77 corresponding to three sides of the four sides thereof are sandwiched between the fourth porous member 392 and the solid electrolyte member 75.

Like the third gas sensor element 207, this fourth gas sensor 307 has a single second gas introduction passage 194 which extends from an outer wall surface to the gas measuring chamber 91.

Notably, the fourth gas sensor element 307 has a two-cell structure (including the oxygen concentration cell 81 and the oxygen pump cell 89) like the above-described gas sensor element 7. The gas measuring chamber 91 of the fourth gas sensor element 307 is formed by the solid electrolyte member 83, the second insulating spacer 193, and the solid electrolyte member 75.

Notably, components of the fourth gas sensor element 307 which have the same configurations as those of the above-described gas sensor element are denoted by the same reference numerals.

Like the above-described as sensor element 7, this fourth gas sensor element 307 can prevent blackening of the solid electrolyte member 83 and the solid electrolyte member 75, and can prevent green breakage of the solid electrolyte member 83 and the solid electrolyte member 75 during manufacture, to thereby prevent cracking of the solid electrolyte member 83 and the solid electrolyte member 75 produced through firing.

Namely, the structure of the gas sensor element is not limited to the structure in which porous members are disposed at the forward and rear ends of a porous electrode in the longitudinal direction (the gas sensor element 7), and there can be employed the structure in which a porous member is disposed along three edges of a porous electrode corresponding to three sides of the four sides thereof (the fourth gas sensor element 307).

Correspondence in wording between claims and the present embodiment will be described below.

The porous electrode 77 and the porous electrode 79 correspond to the pair of electrodes; the porous electrode 85 and the porous electrode 87 correspond to the pair of electrodes; the second insulating spacer 193 corresponds to the dense member; and the gas measuring chamber 91 corresponds to the hollow cavity and the measuring chamber. The fourth porous member 392 corresponds to the porous member; the porous electrode 77 and the porous electrode 87 correspond to the cavity side electrode; and the second diffusion controlling portion 195 corresponds to the diffusion resistance portion.

Figure 16:
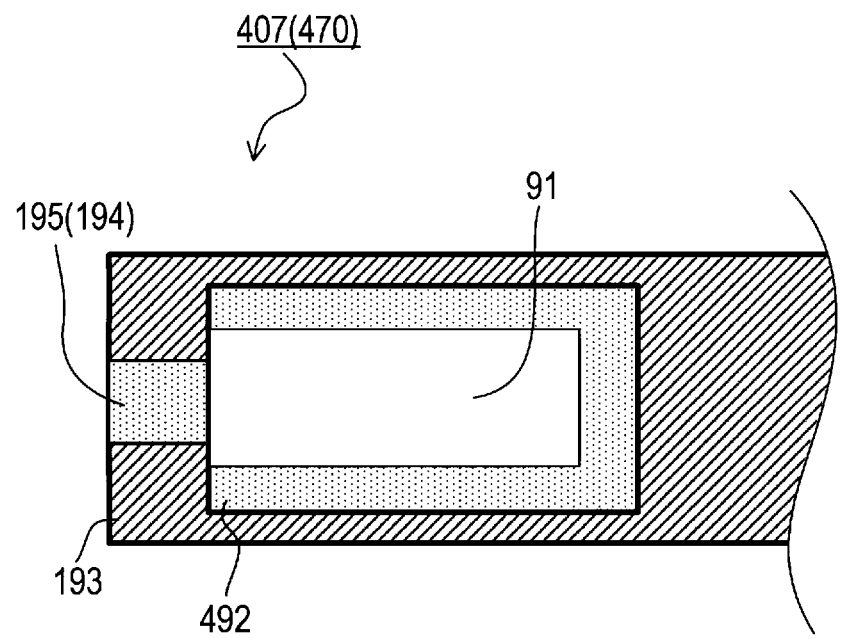
FIG. 16 is a sectional view showing the internal structure of a fifth gas sensor element.

Notably, the fourth gas sensor element 307 may be modified. FIG. 16 shows a fifth gas sensor element 407 which is a modification of the fourth gas sensor element 307 and which has a fifth porous member 492 which also includes three sections.

As shown in FIG. 16, in the fifth gas sensor element 407, the fifth porous member 492 is disposed in the gas measuring chamber 91 of a fifth element body 470 such that the fifth porous member 492 extends along three edges of the porous electrode 87 corresponding to three sides of the four sides thereof; i.e., two sides corresponding to opposite side surfaces of the porous electrode 87 extending in the longitudinal direction and one side corresponding to the rear end of the porous electrode 87 in the longitudinal direction.

Notably, the structure of the gas sensor element is not limited to the structure in which a porous member is disposed along three sides of a porous electrode, the three sides including two sides corresponding to opposite side surfaces of the porous electrode extending in the longitudinal direction and one side corresponding to the forward end of the porous electrode in the longitudinal direction (the fourth gas sensor element 307), and there can be employed the structure in which a porous member is disposed along three sides of a porous electrode, the three sides including the two sides corresponding to opposite side surfaces of the porous electrode and one side corresponding to the rear end of the porous electrode (the fifth gas sensor element 407).

In this case, the fifth porous member 492 corresponds to the porous member.

5. Other Embodiments

While the present invention has been described with reference to the above embodiment, the present invention is not limited thereto, but may be embodied in various other forms without departing from the gist of the invention.

For example, the diffusion resistances of the porous member(s), the porous electrode(s), and the diffusion controlling portion(s) are not limited to the above-described values, and may be set to arbitrary values within a range of numerical value in which the present invention is applicable.

Namely, the diffusion resistances of the porous member(s) and the diffusion controlling portion(s) (diffusion resistance portion) may be set to arbitrary values so long as the diffusion resistance of the porous member(s) is equal to or smaller than the diffusion resistance of the diffusion controlling portion(s) (diffusion resistance portion). Also, the diffusion resistances of the porous electrode(s) (cavity side electrode) and the diffusion controlling portion(s) (diffusion resistance portion) may be set to arbitrary values so long as the diffusion resistance of the porous electrode(s) (cavity side electrode) is larger than the diffusion resistance of the diffusion controlling portion(s) (diffusion resistance portion).

The size of an area in which each porous member overlaps with a cavity side electrode is not limited to that shown in the above-described embodiments. The size of the overlapping area can be freely determined so long as the cavity side electrode can be sandwiched between the porous member and the corresponding solid electrolyte member.

Figure 17:
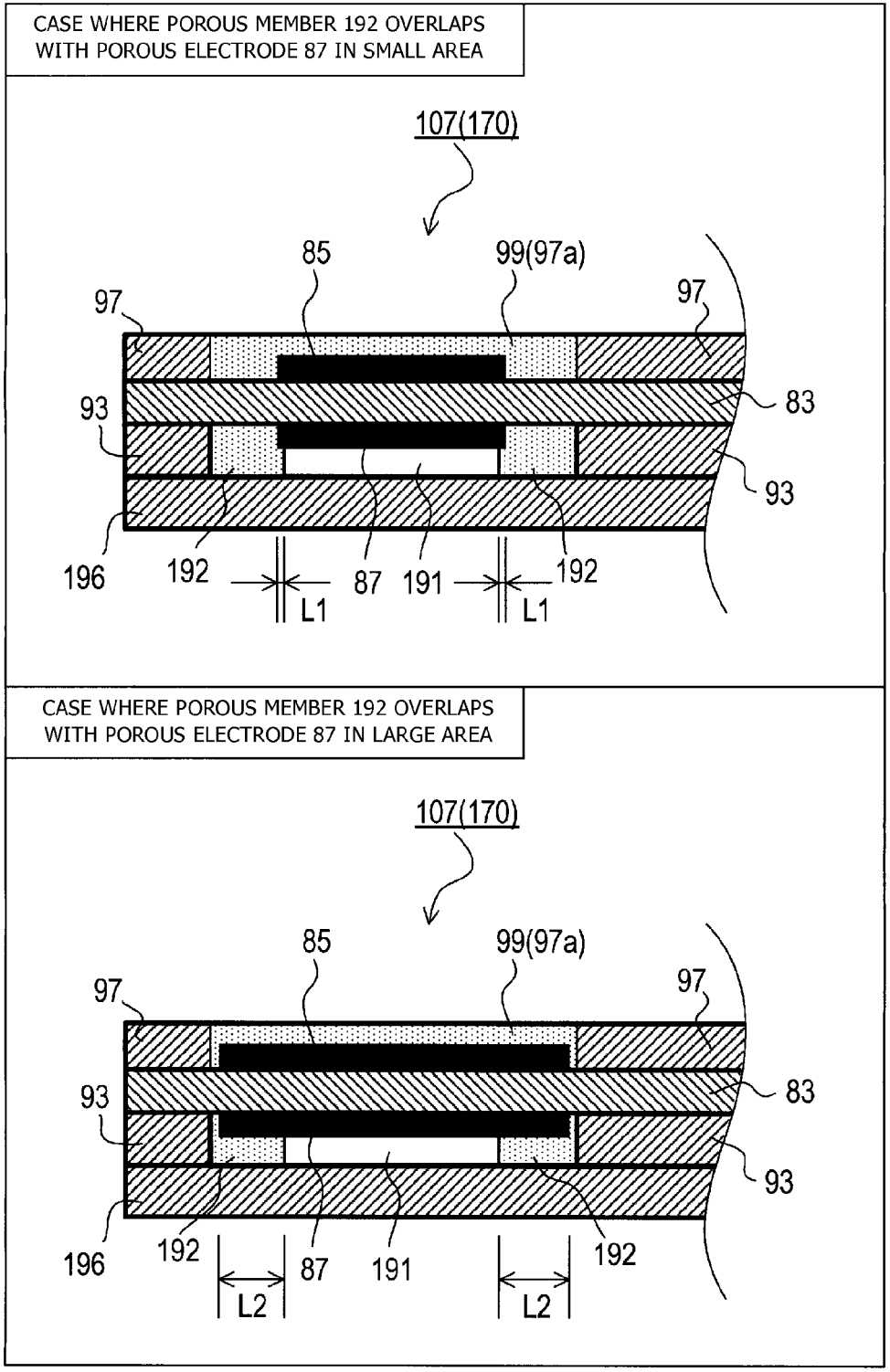
FIG. 17 is an explanatory view used for describing the size of an area in which a second porous member overlaps with a porous electrode.
Figure 18:
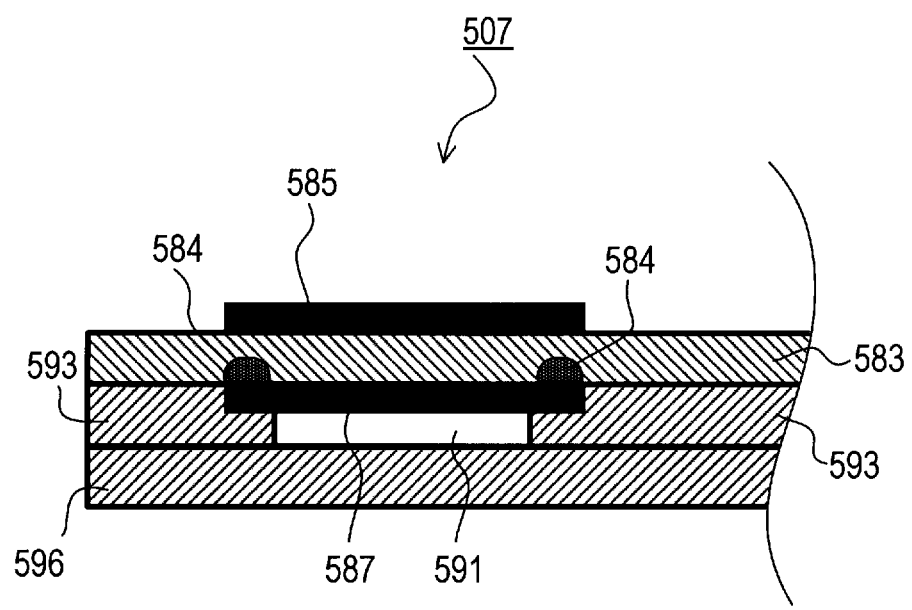
FIG. 18 is an explanatory view used for describing blackening in a conventional gas sensor element.

For example, in the second gas sensor element 107, each second porous member 192 may overlap with the porous electrode 87 in a small area having a dimension L1 shown on the upper side of FIG. 17 or in a large area having a dimension L2 shown on the lower side of FIG. 17. In FIG. 17, the structure in which the second porous member 192 overlaps with the porous electrode 87 in a small area is shown on the upper side, and the structure in which the second porous member 192 overlaps with the porous electrode 87 in a large area is shown on the lower side.

Notably, even in the case where the degree of overlapping between the second porous member 192 and the porous electrode 87 is large, the porous electrode 87 is disposed such that it is separated from the insulating spacer 93 and does not come into contact with the insulating spacer 93.

DESCRIPTION OF REFERENCE NUMERALS

1: air/fuel ratio sensor; 7: gas sensor element; 17: protection layer; 70: element body; 71: element; 73: heater; 75: solid electrolyte member; 77: porous electrode; 79: porous electrode; 81: oxygen concentration cell; 83: solid electrolyte member; 85: porous electrode; 87: porous electrode; 89: oxygen pump cell; 90: detection section; 91: gas measuring chamber; 92: porous member; 93: insulating spacer; 94: gas inlet; 95: diffusion controlling portion; 107: second gas sensor element; 191: atmospheric chamber; 192: second porous member; 193: second insulating spacer; 194: second gas inlet; 195: second diffusion controlling portion; 207: third gas sensor element; 292: third porous member; 307: fourth gas sensor element; 392: fourth porous member; 407: fifth gas sensor element; 492: fifth porous member 492.

What is claimed is:

1. A gas sensor element comprising:
a plate-shaped ceramic solid electrolyte member having a pair of electrodes formed primarily of a metal and disposed on the solid electrolyte member; and
a ceramic dense member layered on the solid electrolyte member and forming at least a portion of a wall surface of a hollow cavity into which gas to be measured or the atmosphere is introduced,
the gas sensor element being adapted to detect a particular gas contained in the gas to be measured, wherein
one of the pair of electrodes is a cavity side electrode disposed to face the hollow cavity;
the cavity side electrode is spaced from the wall surface of the hollow cavity; and
at least one ceramic porous member is provided in the hollow cavity, the ceramic porous member partially covering the cavity side electrode such that the cavity side electrode is partially exposed to the hollow cavity and extending from a position on the cavity side electrode, beyond an end or peripheral edge portion of the cavity side electrode, to a position on a surface of the solid electrolyte member exposed to the hollow cavity.

2. A gas sensor element according to claim 1, wherein the ceramic porous member for partially covering the cavity side electrode comprises two sections which are provided at each of two positions corresponding to opposite ends of the cavity side electrode in a longitudinal direction thereof, and the opposite ends of the cavity side electrode are sandwiched between the sections of the ceramic porous member and the solid electrolyte member.

3. A gas sensor element according to claim 1, wherein the ceramic porous member for partially covering the cavity side electrode is formed by at least two separate ceramic porous members which are provided at each of two positions corresponding to opposite ends of the cavity side electrode in a longitudinal direction thereof, and the opposite ends of the cavity side electrode are sandwiched between the ceramic porous member and the solid electrolyte member.

4. A gas sensor element according to claim 1, further comprising a porous diffusion resistance portion provided in a gas introduction passage extending from an outer wall surface of the gas sensor element to the hollow cavity, wherein the ceramic porous member has a diffusion resistance equal to or smaller than that of the porous diffusion resistance portion.

5. A gas sensor element according to claim 4, wherein the cavity side electrode is a porous electrode, and has a diffusion resistance equal to or larger than that of the porous diffusion resistance portion.

6. A gas sensor element according to claim 1, wherein the hollow cavity is a measuring chamber into which the gas to be measured is introducible.

7. A gas sensor element according to claim 1, wherein the hollow cavity is an atmospheric chamber into which the atmosphere is introducible.

8. A gas sensor element according to claim 1, wherein the ceramic porous member only covers the peripheral edge portion of the cavity side electrode while leaving a central portion of the cavity side electrode uncovered.

9. A gas sensor comprising a gas sensor element for detecting a particular gas contained in gas to be measured, wherein the gas sensor element is a gas sensor element according to claim 1.

* * * * *